(12) United States Patent
Smith et al.

(10) Patent No.: US 9,529,008 B2
(45) Date of Patent: Dec. 27, 2016

(54) SAMPLING PROBES, SYSTEMS, APPARATUSES, AND METHODS

(75) Inventors: Wesley Smith, Junction City, OR (US);
Glen Davis, Junction City, OR (US);
John Jackson, Oceanside, CA (US);
Gregory Kaduchak, Eugene, OR (US);
Michael Ward, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 772 days.

(21) Appl. No.: 13/411,337

(22) Filed: Mar. 2, 2012

(65) Prior Publication Data
US 2012/0227471 A1    Sep. 13, 2012

Related U.S. Application Data

(60) Provisional application No. 61/449,025, filed on Mar. 3, 2011, provisional application No. 61/490,451, filed on May 26, 2011.

(51) Int. Cl.
*G01N 1/10* (2006.01)
*G01N 35/10* (2006.01)

(52) U.S. Cl.
CPC .................. *G01N 35/1011* (2013.01)

(58) Field of Classification Search
CPC ...................................................... G01N 1/10
USPC .................. 73/864, 864.01, 864.02, 864.11, 864.13, 73/864.18
See application file for complete search history.

(56) References Cited

U.S. PATENT DOCUMENTS

| D319,102 S | 8/1991 | Futatsuka et al. |
| D387,164 S | 12/1997 | Barnett et al. |
| 5,998,218 A * | 12/1999 | Conley ................. B01L 3/0224 422/63 |
| 6,170,343 B1 * | 1/2001 | Conley ................. B01L 3/0224 73/864.18 |
| 6,305,482 B1 * | 10/2001 | Aumann ................. E21B 25/08 175/20 |
| D456,523 S | 4/2002 | Waluszko et al. |

(Continued)

FOREIGN PATENT DOCUMENTS

| DE | 102004025588 | 12/2005 |
| EP | 1726963 | 11/2006 |

(Continued)

OTHER PUBLICATIONS

Biocompare,"Cyan ADP Flow Cytometer from Beckman Coulter", www.biocompare.com/12328-Flow-Cytometer-Flow-Cytometer-Systems/2760260-Cyan-ADP, Jan. 10, 2013, 1.

(Continued)

*Primary Examiner* — Michael A Lyons
*Assistant Examiner* — Hoang Nguyen
(74) *Attorney, Agent, or Firm* — Life Technologies Corporation

(57) ABSTRACT

A sampling system is provided. The sampling system includes a housing. Mounted to the housing is a Hall effect sensor. A probe configured to contact a sample is inserted into the housing. The probe includes an elongated portion and a restorative spring inserted onto the elongated portion of the probe. The restorative spring provides sufficient restorative force to return the probe to a relaxed position. The Hall effect sensor is configured to sense a field strength generated by the proximity of the restorative spring of the probe in the extended position.

8 Claims, 28 Drawing Sheets

(56) References Cited

U.S. PATENT DOCUMENTS

| | | | |
|---|---|---|---|
| 6,669,909 B2* | 12/2003 | Shvets | B01L 3/0265 137/487.5 |
| 7,340,957 B2 | 3/2008 | Kaduchak et al. | |
| 7,585,468 B2* | 9/2009 | Jaghuber | B01L 3/0224 422/561 |
| D634,442 S | 3/2011 | Tajima et al. | |
| D662,209 S | 6/2012 | Swanek et al. | |
| D663,429 S | 7/2012 | Swanek | |
| D668,833 S | 10/2012 | De Togni | |
| 8,570,029 B2* | 10/2013 | Andres | B01L 3/0217 324/207.2 |
| D698,038 S | 1/2014 | Davis et al. | |
| 2008/0245709 A1 | 10/2008 | Kaduchak et al. | |
| 2008/0245745 A1 | 10/2008 | Ward et al. | |
| 2009/0029870 A1 | 1/2009 | Ward et al. | |
| 2009/0042239 A1 | 2/2009 | Ward et al. | |
| 2009/0042310 A1 | 2/2009 | Ward et al. | |
| 2009/0045107 A1 | 2/2009 | Ward et al. | |
| 2009/0048805 A1 | 2/2009 | Kaduchak et al. | |
| 2009/0050573 A1 | 2/2009 | Ward et al. | |
| 2009/0053686 A1 | 2/2009 | Ward et al. | |
| 2009/0158823 A1 | 6/2009 | Kaduchak et al. | |
| 2009/0162887 A1 | 6/2009 | Kaduchak et al. | |
| 2009/0178716 A1 | 7/2009 | Kaduchak et al. | |
| 2010/0092683 A1* | 4/2010 | Ermantraut | G01N 35/1011 427/424 |
| 2010/0291668 A1* | 11/2010 | Bertrand | B01L 3/502 435/287.2 |
| 2011/0134426 A1 | 6/2011 | Kaduchak et al. | |
| 2012/0115744 A1* | 5/2012 | Raymond | C12Q 1/6811 506/9 |

FOREIGN PATENT DOCUMENTS

| | | |
|---|---|---|
| JP | 03183958 | 9/1991 |
| JP | 10-332733 | 12/1998 |
| JP | 2002-062302 | 2/2002 |
| JP | 2010-203773 | 9/2010 |
| WO | 91/16675 | 10/1991 |
| WO | 99/15875 | 4/1999 |
| WO | 99/32870 | 7/1999 |
| WO | 01/57490 | 8/2001 |
| WO | 2008/034914 | 3/2008 |
| WO | 2011/104986 | 9/2011 |
| WO | 2012/119118 | 9/2012 |

OTHER PUBLICATIONS

Kolling Institute of Medical Res, www.kolling.usyd.edu.au/core-facilities/flow-cytometry/index.php, Jan. 10, 2013, 1.

Northwestern University, www.basic.northwestern.edu/sharedresources/flowcytometry/instr.html, Jan. 10, 2013, 1.

PCT/US2012/027580, "Invitation to Pay Additional Fees and Partial International Search Report mailed", Jun. 1, 2012, 9 pgs.

STRATEDIGM, "Flow Cytometer", *BD LSR II & BD Fortessa Alternativese*, Flow Cytometer Analyzers, www.stratedigm.com/instrumentation/, Jan. 11, 2013, 1.

SG 201306626-1, Examination Report mailed on May 8, 2015, 11 Pages.

PCT/US2012/027580, International Search Report and Written Opinion mailed Nov. 25, 2015, 18 pgs.

PCT/US2012/027580, International Preliminary Report on Patentability mailed Dec. 15, 2015, 12 pgs.

\* cited by examiner

SAMPLING PROBES, SYSTEMS, APPARATUSES, AND METHODS

CROSS-REFERENCE TO RELATED APPLICATIONS

This application claims the benefit of priority of U.S. provisional application Ser. Nos. 61/449,025, filed Sep. Mar. 3, 2011, and 61/490,451, filed May 26, 2011, both of which are incorporated herein by reference in their entirety. This application is related to U.S. design patent application Ser. No. 29/386,708, filed on Mar. 3, 2011.

BACKGROUND

The present application generally relates to sampling probes, systems, apparatuses, and methods for hi-throughput flow cytometry and/or for processing samples in batches.

Systems and apparatuses utilizing sample probes are used in numerous fields, including academic and industrial research, bioproduction, and pharmaceutical industries, for example. In general, in these fields, a large numbers of samples need to be processed rapidly and efficiently.

However, previously, sample probes required separate manipulation and handling of each sample, even when processing multiple samples. Furthermore, extended sample drawing probes often increased the risk of damage to such probes.

In fields such as in flow cytometry, genetic sequencing, drug discovery, and proteomics, for example, improvements to sample probe systems are desired.

SUMMARY

According to embodiments described herein, there are provided probes, systems, apparatuses, and methods that help address the aforementioned needs.

According to an exemplary embodiment of the present teachings, there is provided a sample probe with a built-in obstacle detection mechanism that may reduce costs and increase time savings by reducing both instrument downtime and increasing probe position accuracy and durability.

According to an exemplary embodiment of the present teachings, there is provided a compliant sample probe with position feedback that minimizes damage to the probe in cases of collisions and calibrates the location of the probe in three-dimensional space.

According to an exemplary embodiment of the present teachings, there is provided a magnet-based probe with opposing magnets that provide force to push the probe back to a normal state after it has been depressed in contact with another object, and a Hall effect sensor that detects a change in magnetic field when the magnets are pushed closer to each other as the probe is depressed from its relaxed position.

According to an exemplary embodiment of the present teachings, there is provided a sampling probe, including: a fitting; an elongated portion extending from the fitting; and a restorative spring including at least one magnet inserted onto the elongated portion.

According to various embodiments described herein, the restorative spring may include a single magnet, three magnets, or a metal spring, for example. It should be recognized that the restorative spring according to various embodiments described herein may be any object or assembly that can provide sufficient restorative force to return the probe to a relaxed position.

According to an exemplary embodiment of the present teachings, there is provided a sampling system, including: a housing; a Hall effect sensor mounted onto the housing; and a sampling probe inserted into the housing, the sampling probe including an elongated portion and a plurality of magnets inserted onto the elongated portion.

According to an exemplary embodiment of the present teachings, there is provided a plate sampling apparatus, including: a sampling compartment including a tray configured to receive a sample plate configured to include a plurality of samples; and a probe configured to obtain a sample from the sample plate, the probe including a fitting, an elongated portion extending from the fitting, and a restorative spring including a plurality of magnets inserted onto the elongated portion.

According to an exemplary embodiment of the present teachings, there is provided a hi-throughput cytometry system, including: a flow cytometer configured to acoustically focus a sample in a flowing fluid; and a plate sampler in fluidic communication with the flow cytometer, the plate sampler including: a sampling compartment including a tray configured to receive a sample plate configured to include a plurality of samples, and a probe configured to obtain a sample from the sample plate, the probe including a fitting, an elongated portion extending from the fitting, and a restorative spring including a plurality of magnets inserted onto the elongated portion.

According to an exemplary embodiment of the present teachings, there is provided a method for obtaining a sample, including: sampling a sample plate including one or more samples in a plate sampler; moving toward the sample plate a probe including a fitting, an elongated portion extending from the fitting, and a restorative spring including at least two opposing magnets inserted onto the elongated portion; sensing a field strength generated by the opposing magnets in the extended position using a Hall effect sensor; detecting an increase in the field strength generated by the opposing magnets using the Hall effect sensor; stopping the motion of the probe toward the sample plate; and obtaining a sample from the one or more samples in the sample plate using a probe including a fitting, an elongated portion extending from the fitting, and a restorative spring including a plurality of magnets inserted onto the elongated portion.

According to an exemplary embodiment of the present teachings, there is provided a method for obtaining a sample, including: sampling a sample plate including one or more samples in a plate sampler; moving toward the sample plate a probe including a fitting, an elongated portion extending from the fitting, a restoration restorative spring, and a magnet; sensing a field strength generated by the proximity of the magnet in the extended position using a Hall effect sensor; detecting an increase in the field strength generated by the magnet proximity using the Hall effect sensor; stopping the motion of the probe toward the sample plate; and obtaining a sample from the one or more samples in the sample plate using probe assembly.

According to an exemplary embodiment of the present teachings, there is provided a method for making a sampling probe, including: providing a fitting; assembling onto the fitting an elongated portion extending from the fitting; and inserting onto the elongated portion a restorative spring including a plurality of rare earth magnets.

According to an exemplary embodiment of the present teachings, there is provided a plate sampler apparatus, including: a loading compartment including a sample probe and a tray, the tray being configured to receive a sample plate configured to include a plurality of samples; a fluidic compartment configured to receive one or more fluid containers; a first access door configured to allow access to the loading compartment; and a second access door configured to allow access to the fluidic compartment.

According to another exemplary embodiment of the present teachings, there is provided a hi-throughput cytometry system, including: a flow cytometer configured to acoustically focus a sample in a flowing fluid; and a plate sampler in fluidic communication with the flow cytometer.

According to an exemplary embodiment of the present teachings, there is provided a hi-throughput cytometry system, including: a flow cytometer; and a plate sampler in fluidic communication with the flow cytometer, the plate sampler including: a sample probe and a tray, the tray being configured to receive a sample plate configured to include a plurality of samples; a fluidic compartment configured to receive one or more fluid containers; a first access door configured to allow access to the loading compartment; and a second access door configured to allow access to the fluidic compartment.

According to an exemplary embodiment of the present teachings, there is provided a hi-throughput cytometry system, including: a flow cytometer; and a plate sampler in fluidic communication with the flow cytometer, the plate sampler including an actuation mechanism configured to move a tray toward a top surface of the plate sampler such that a sample plate may be loaded onto the tray from above the plate sampler.

The foregoing general description and the following detailed description are exemplary only and are not limiting in any way of the scope of the present teachings. Other embodiments or variations upon embodiments specifically discussed herein, including various combinations of features of embodiments discussed herein, may be realized from the following detailed description or may be learned by practice of the present teachings.

BRIEF DESCRIPTION OF THE DRAWINGS

The accompanying drawings illustrate various exemplary embodiments of the invention. The drawings are exemplary only and are not in any way limiting of the scope of the invention.

DETAILED DESCRIPTION

Figure 1:
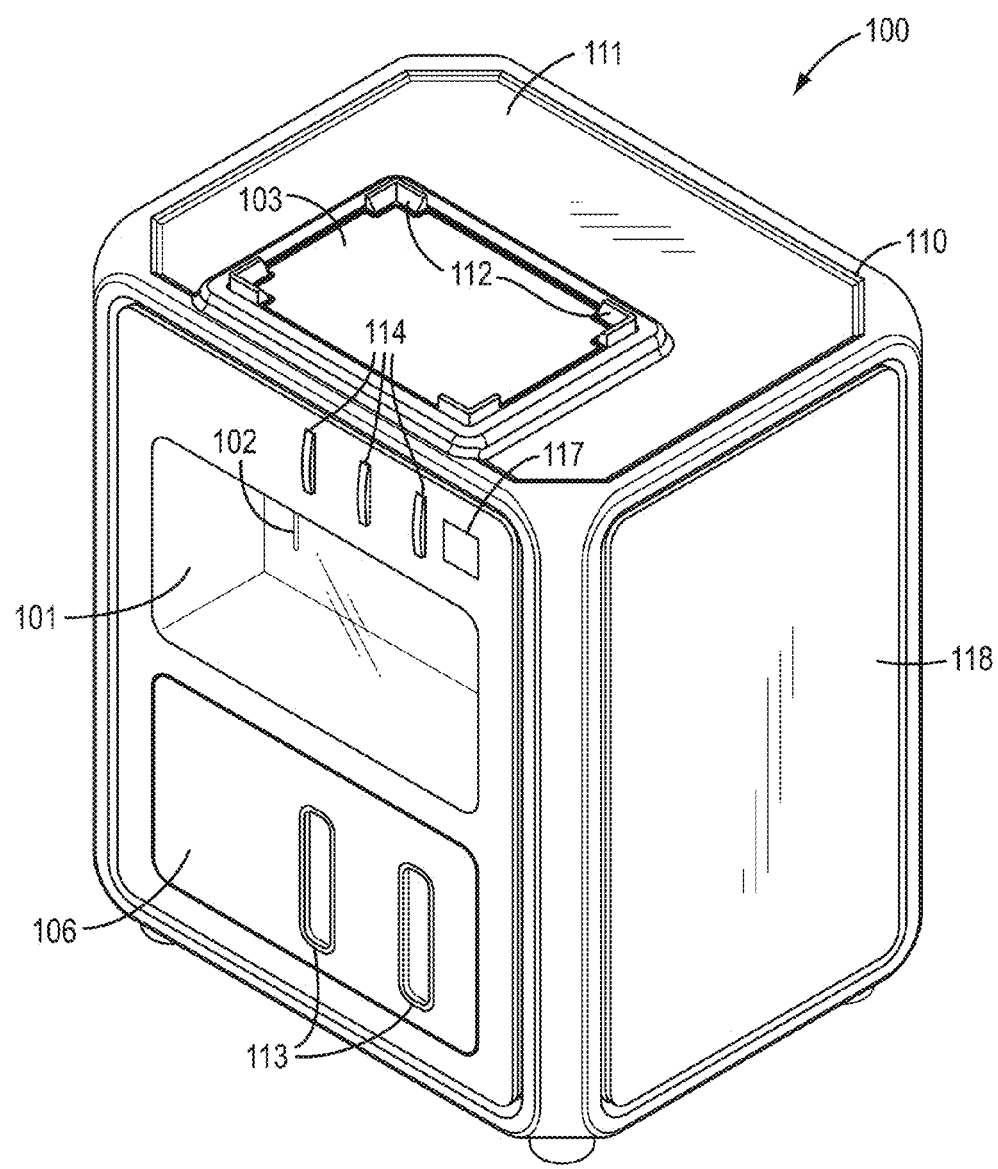
FIG. 1 is a perspective view of an exemplary plate sampler.
Figure 2:
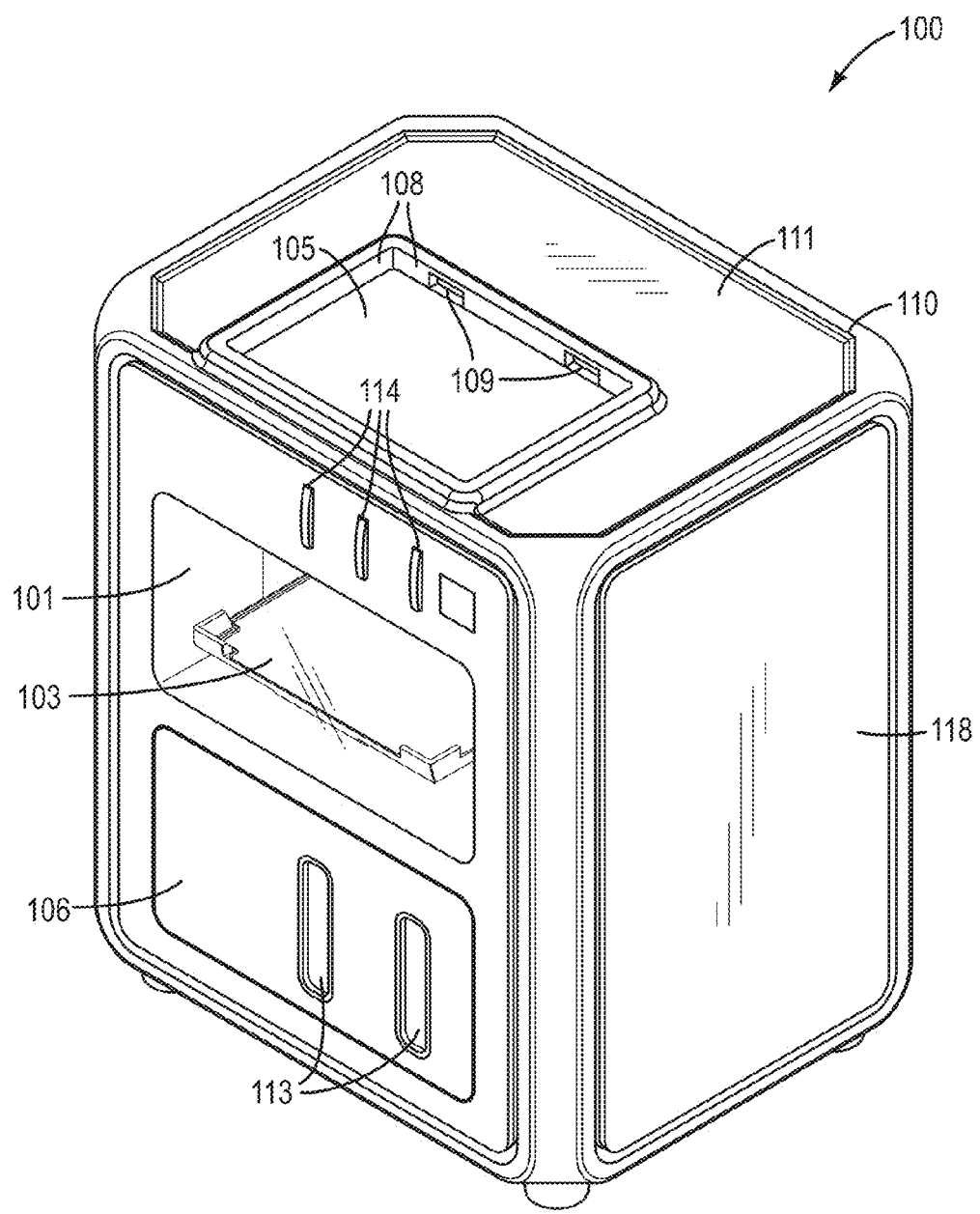
FIG. 2 is another perspective view of the exemplary plate sampler set forth in FIG. 1.
Figure 3:
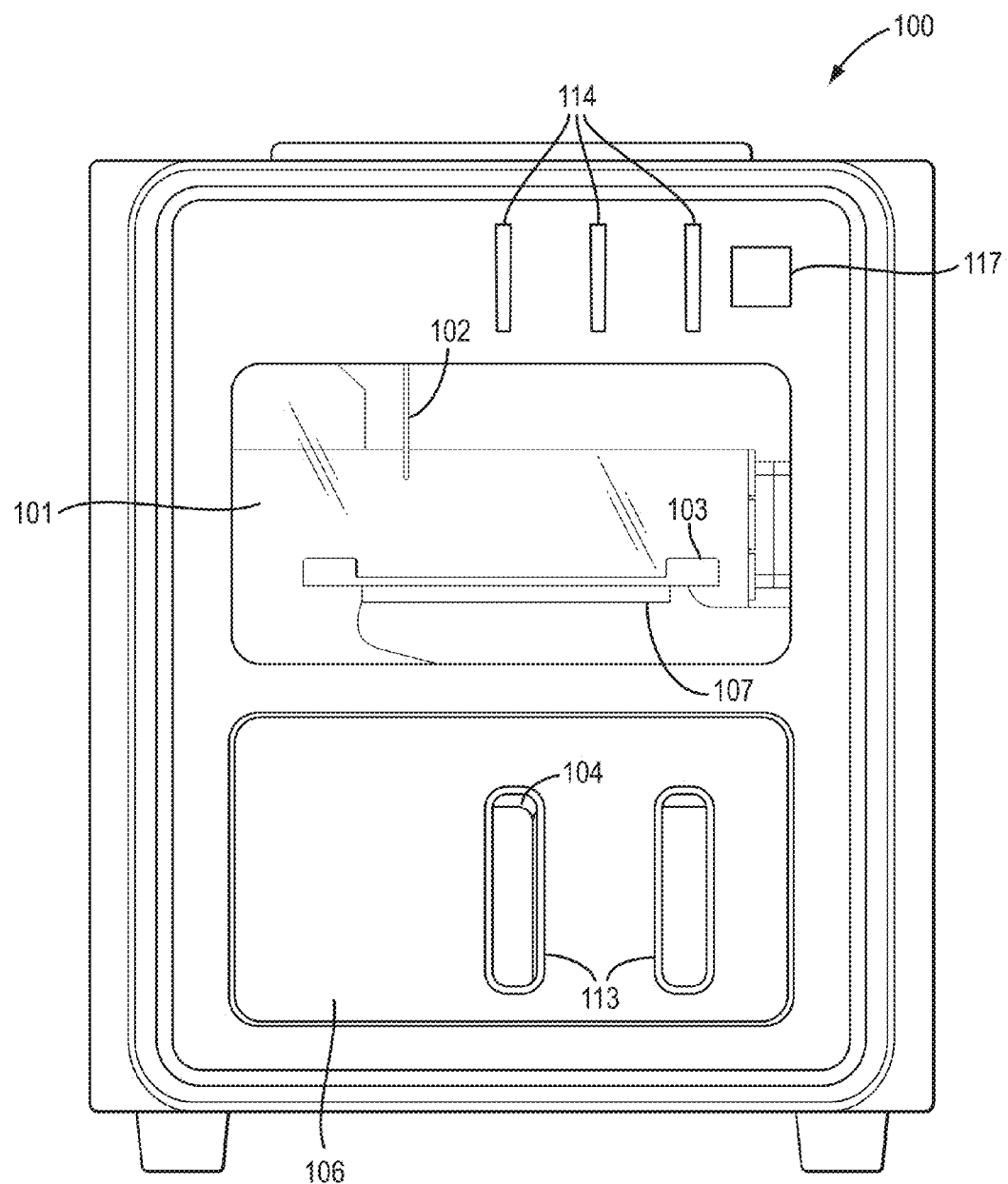
FIG. 3 is a front view of the exemplary plate sampler set forth in FIG. 1.
Figure 4:
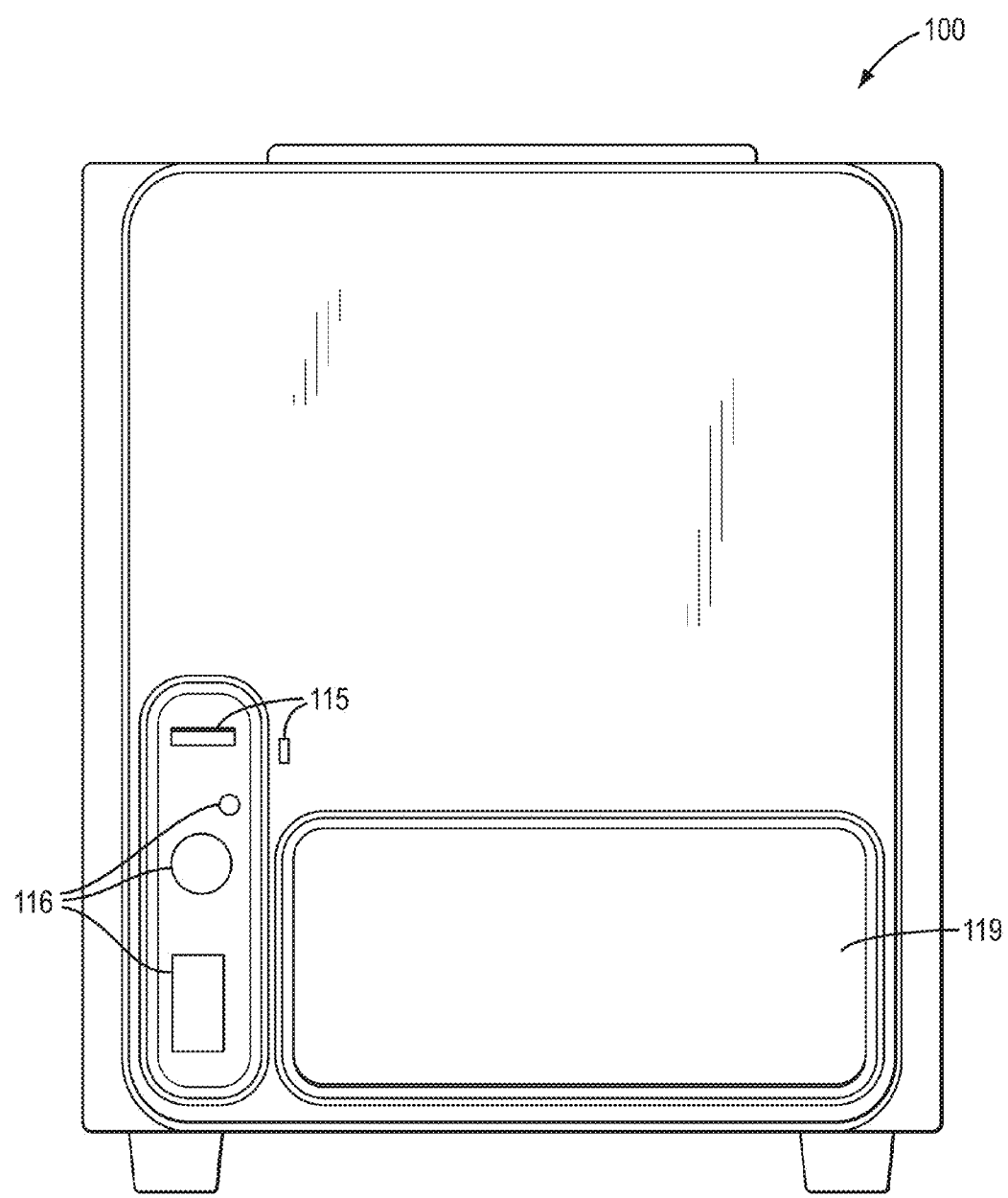
FIG. 4 is a back view of the exemplary plate sampler set forth in FIG. 1.
Figure 5:
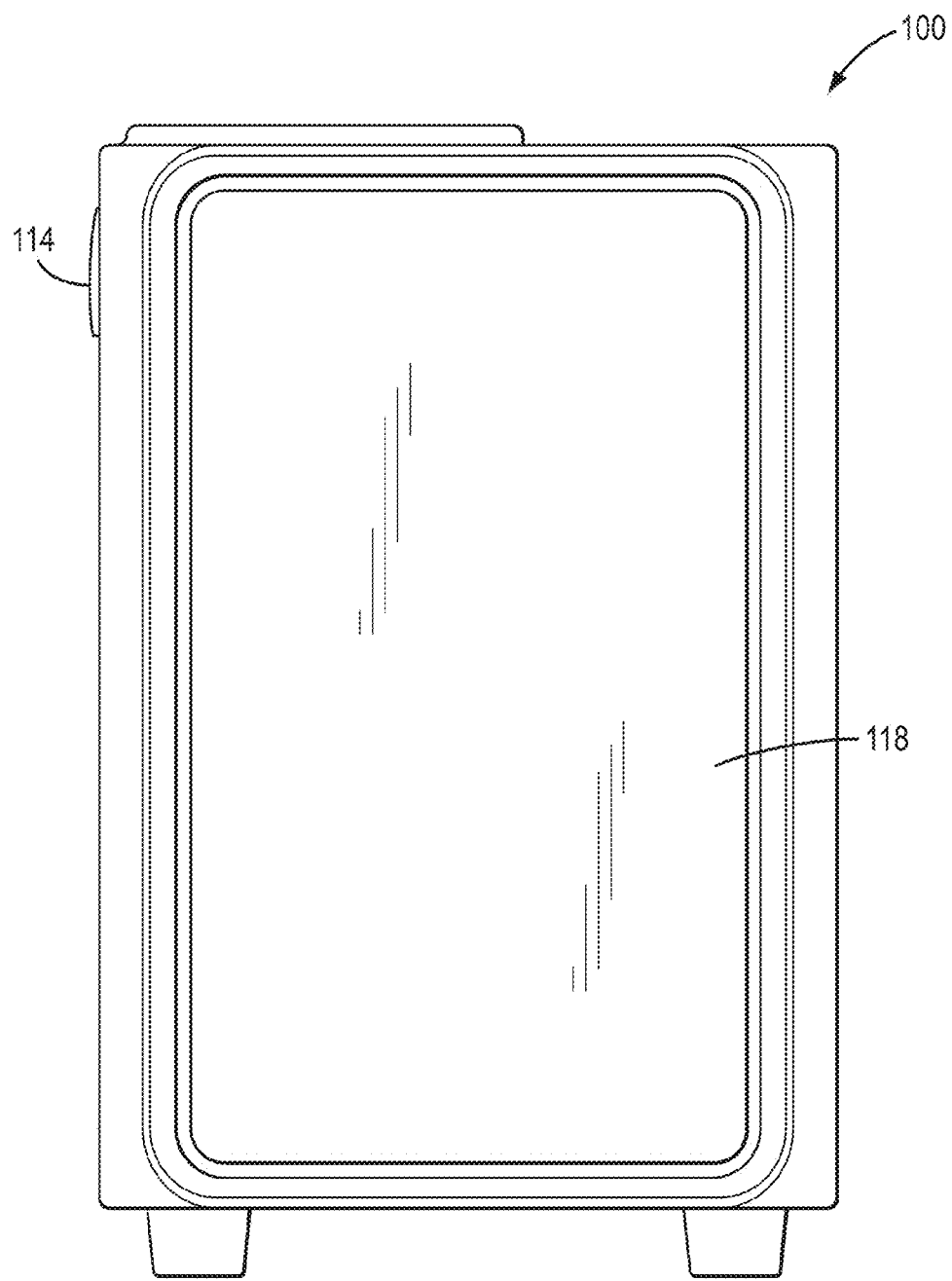
FIG. 5 is a side view of the exemplary plate sampler set forth in FIG. 1.
Figure 6:
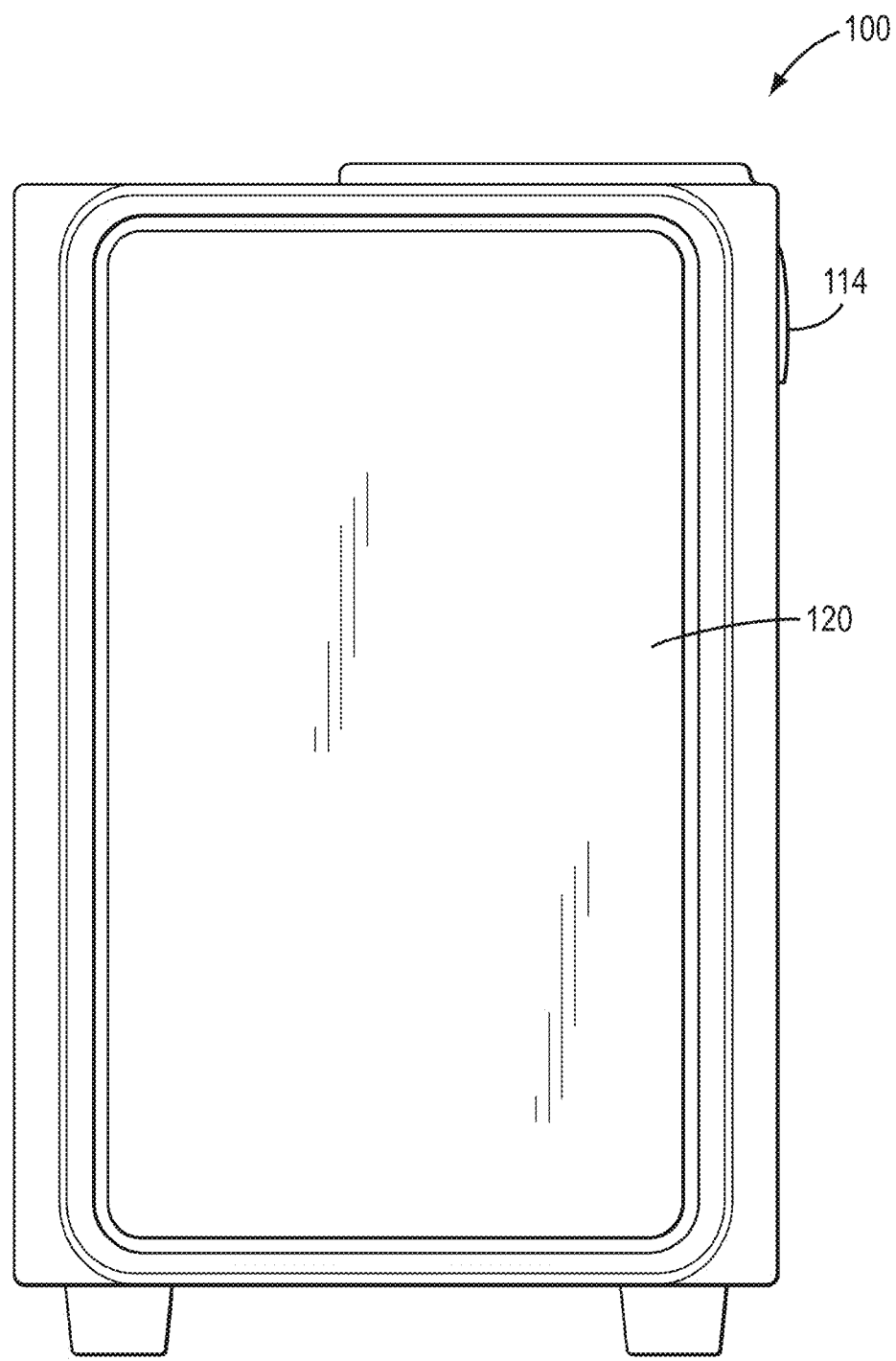
FIG. 6 is another side view of the exemplary plate sampler set forth in FIG. 1.
Figure 7:
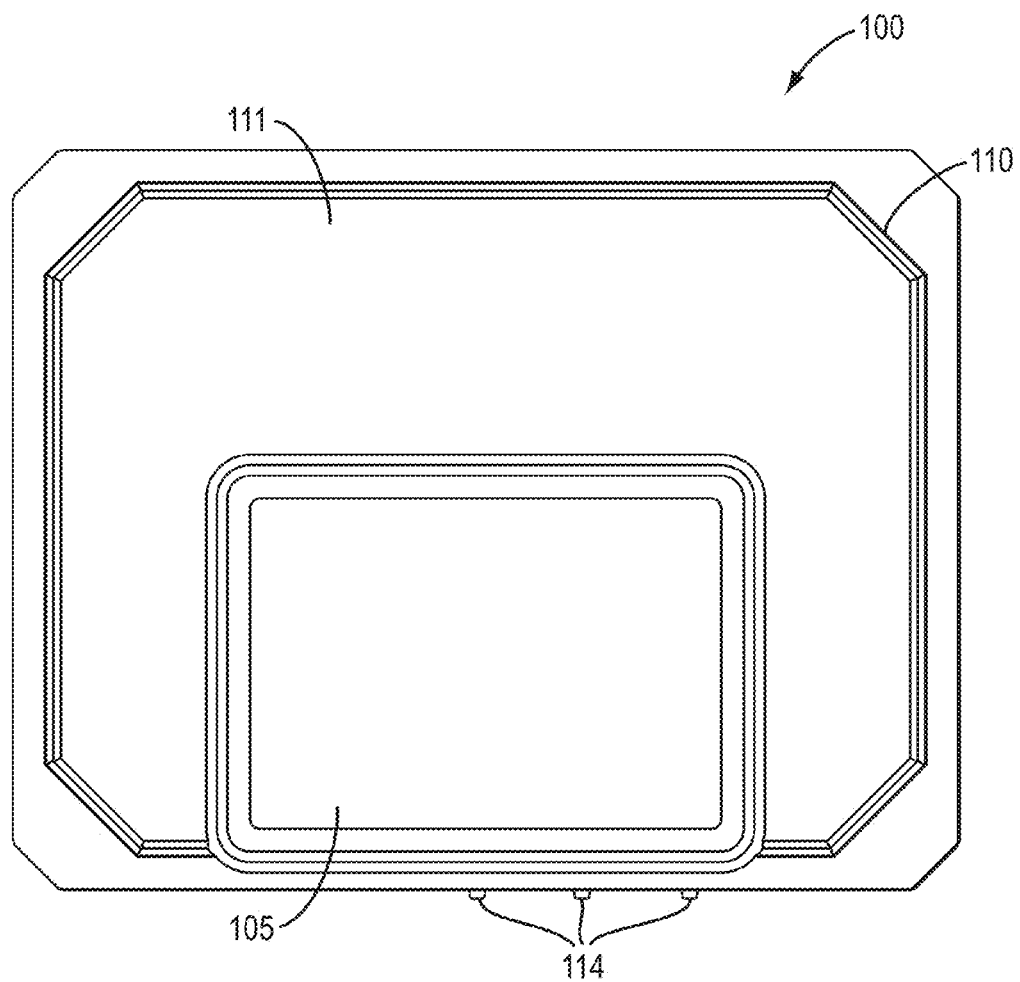
FIG. 7 is a top view of the exemplary plate sampler set forth in FIG. 1.
Figure 8:
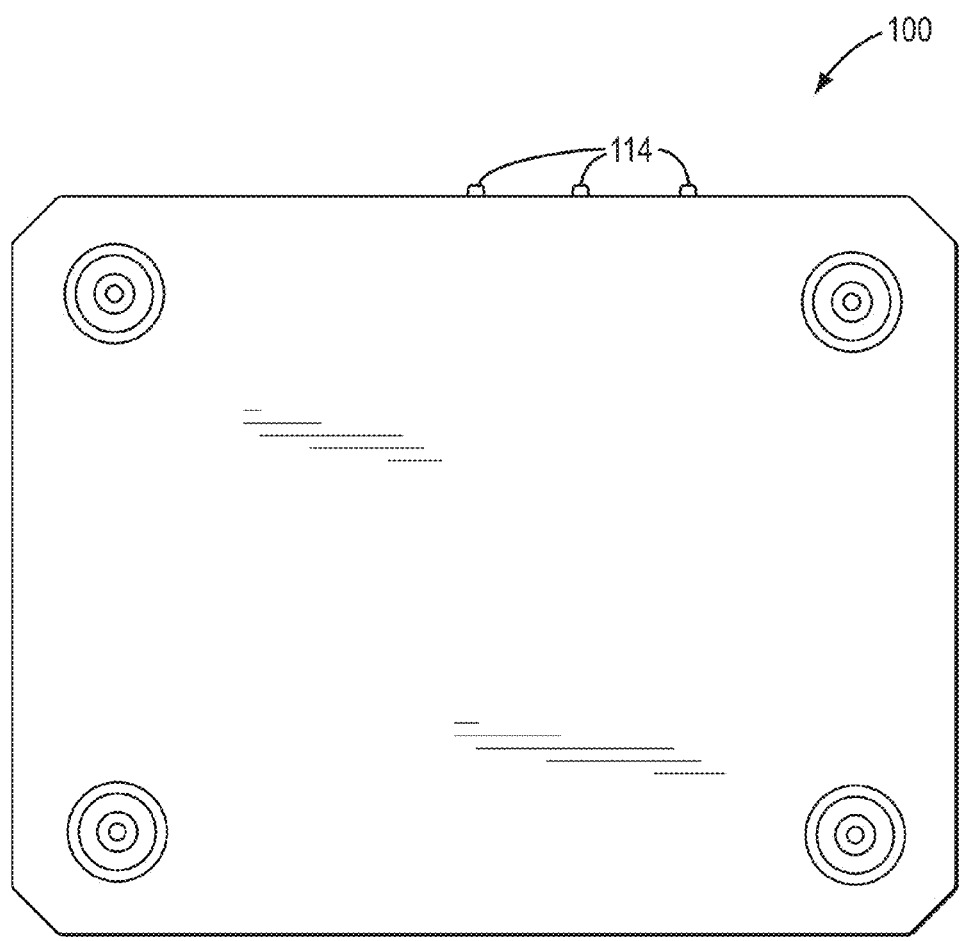
FIG. 8 is a bottom view of the exemplary plate sampler set forth in FIG. 1.

According to an exemplary embodiment of the present teachings, there is provided a plate sampler apparatus, including: a loading compartment including a sample probe and a tray, the tray being configured to receive a sample plate configured to include a plurality of samples; a fluidic compartment configured to receive one or more fluid containers; a first access door configured to allow access to the loading compartment; and a second access door configured to allow access to the fluidic compartment.

In such an apparatus, the loading compartment may further include an actuation mechanism configured to move the tray. The actuation mechanism may be configured to move the tray, when the first access door is opened, along a direction substantially perpendicular to a direction of gravity between a first position located within the loading compartment and a second position located at least partly outside the loading compartment such that a sample plate may be loaded onto the tray from a side of the apparatus by a user of the apparatus or by robotic machinery. Alternatively, the actuation mechanism may be configured to move the tray, when the first access door is opened, along a direction substantially parallel to a direction of gravity between a first position located within the loading compartment and a second position located at least partly outside the loading compartment such that a sample plate may be loaded onto the tray from above the apparatus by a user of the apparatus or by robotic machinery.

One or more side portions of the first access door may include one or more indentations configured to hold the tray in place in the second position. A top surface of the apparatus surrounding the first access door may include a recessed area configured to contain spilled fluid. The tray may include a plurality of protruding corners configured to hold a sample plate in place within the tray. The first access door may be arranged within a top surface of the apparatus. The second access door may include one or more windows allowing a user to monitor a fluid level in one or more fluid containers received in the fluidic compartment. The apparatus may further include a plurality of LED indicators. The apparatus may also further include a data transfer port configured to be connected directly to an acoustic flow cytometer or to a computer in communication with an acoustic flow cytometer or to robotic machinery at least partly controlling the apparatus.

FIGS. 1-8 illustrate various views of an exemplary plate sampler 100 according to an embodiment of the present invention.

The plate sampler 100 may include a sampling compartment 101, which may include a sample probe 102 and a tray 103. The tray 103 may be configured to receive a sample plate configured to receive a plurality of samples, and may include one or more protruding corners 112 configured to hold the sample plate in place.

The sample plate may be any type of sample plate known in the art. Preferably, the sample plate is a 96-well or 384-well sample plate. The sampling compartment 101 may further include an actuation mechanism 107 configured to move the tray 103. The plate sampler 100 may also include a fluidic compartment 104, which may be configured to receive one or more fluid containers. The plate sampler 100 may also include a first access door 105 configured to allow access to the sampling compartment 101 and a second access door 106 configured to allow access to the fluidic compartment 104.

The first access door 105 may be arranged in a top surface 110 of the plate sampler 100, which is especially useful for use with robot or robotic machinery configured to manipulate sample plates. The first access door 105 may be a door that opens by sliding into the top surface 110 or by rotating about one or more hinge points, and it may include a translucent material or a material substantially preventing light emitted at one or more selected wavelength ranges from reaching the samples in the sample plate, for example. The first access door 105 may also have one or more side portions 108 including one or more indentations or registration points 109 configured to hold the tray 103 in place.

The top surface 110 of the plate sampler may include a recessed area 111 around the first access door 105 that may be configured to contain spilled fluid. Finally, the plate sampler 100 may include one or more LED indicators 114, one or more data transfer ports 115, one or more fluid and/or power ports and/or switches 116, one or more buttons 117, and/or one or more access panels 118-120.

FIGS. 9-16 illustrate various views of another exemplary plate sampler 200 according to an embodiment of the present invention. The plate sampler 200 may include a sampling compartment 201, which may include a sample probe 202 and a tray 203. The tray 203 may be configured to receive a sample plate configured to receive a plurality of samples, and may include one or more protruding corners configured to hold the sample plate in place. The sample plate may be any type of sample plate known in the art. For example, the sample plate may be a 96-well, 384-well, 10,000-well, 12,000-well, or 30,000-well sample plate. The sample plate may also contain sample areas that are through-holes.

The sampling compartment 201 may further include an actuation mechanism 207 configured to move the tray 103. The plate sampler 200 may also include a fluidic compartment 204, which may be configured to receive one or more fluid containers. The plate sampler 200 may also include a first access door 205 configured to allow access to the sampling compartment 201 and a second access door 206 configured to allow access to the fluidic compartment 204. The first access door 205 may be arranged in a side or front surface of the plate sampler 200, may be a door that opens by sliding into the side or front surface or by rotating about one or more hinge points, and/or may include a translucent material or a material substantially preventing light emitted at one or more selected wavelength ranges from reaching the samples in the sample plate, for example. The top surface of the plate sampler 200 may be flat and may include a recessed area configured to contain spilled fluid. Finally, the plate sampler 200 may include one or more LED indicators 214, one or more data transfer ports 215, one or more fluid and/or power ports and/or switches 216, one or more buttons 217, and/or one or more access panels 218-220. Plate sampler 200 may also include a touch screen capable of displaying a user interface.

Figure 22A:
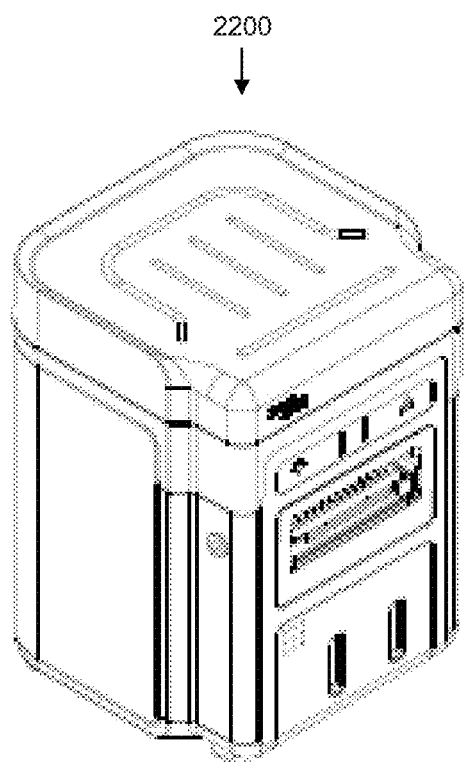
FIGS. 22A-22C illustrates another exemplary embodiment of a plate sampler.
Figure 22B:
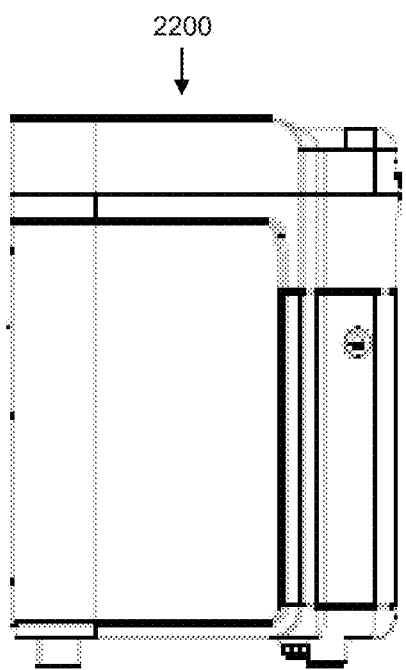
Figure 22C:
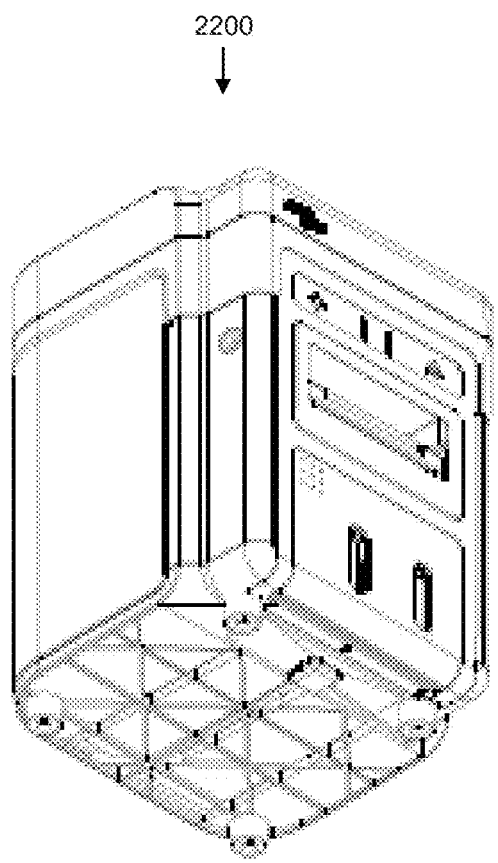

FIGS. 22A-22C illustrate yet another embodiment of a plate sampler 2200. FIG. 22A illustrates a perspective front view of plate sampler 2200. FIG. 22B illustrates another perspective side view of plate sampler 2200. FIG. 22C illustrates a perspective bottom view of plate sampler 2200.

Figure 17:
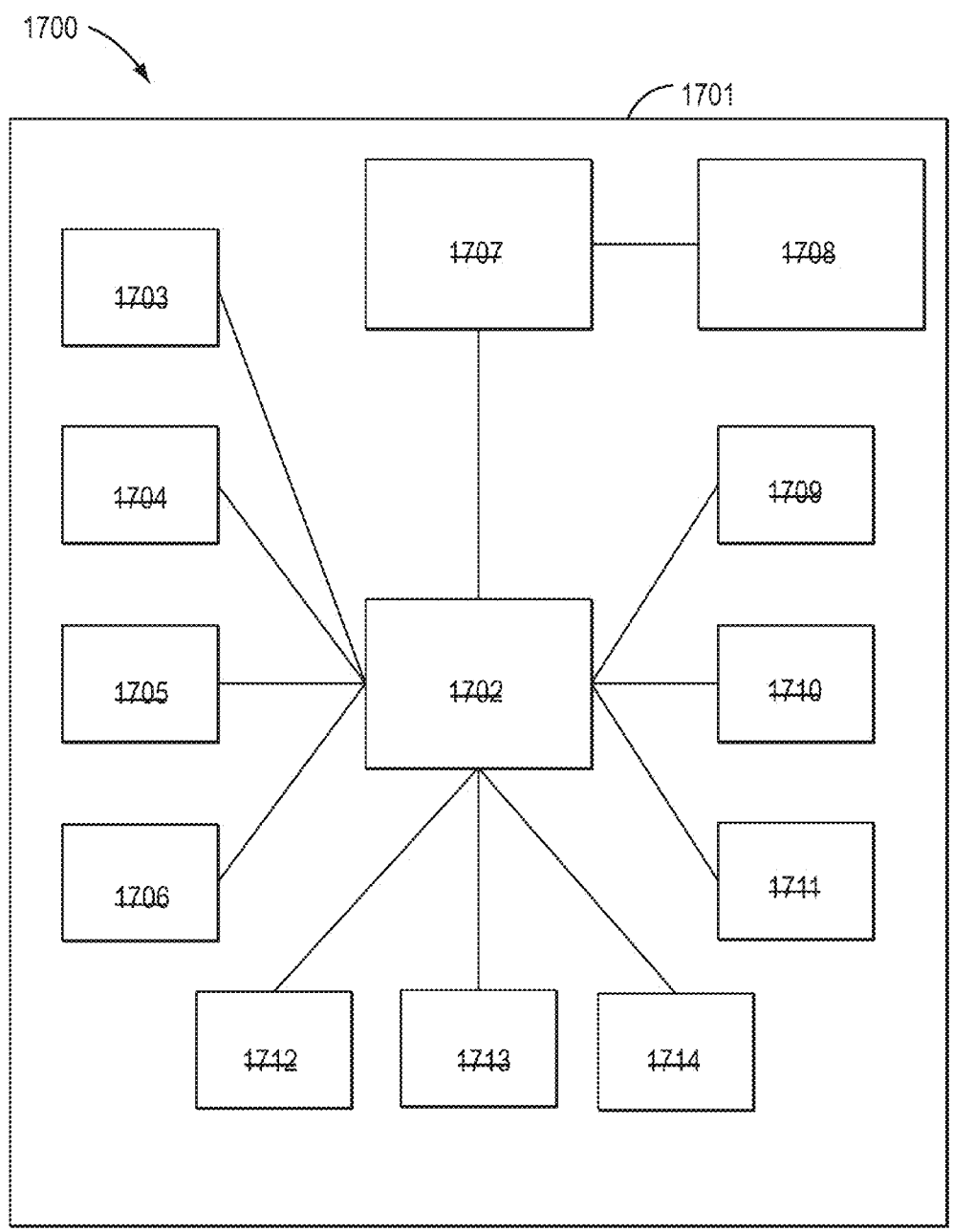
FIG. 17 is a schematic diagram of exemplary components of an embodiment of a plate sampler.

FIG. 17 is a schematic diagram of exemplary components of a plate sampler 1700 according to an embodiment of the present invention. The plate sampler 1700 may include an enclosure 1701 including a controller board 1702 in communication with one or more other components, which may include one or more fluid pumps 1703, one or more fluid bottle sensors 1704, one or more fluid bottle LEDs 1705, one or more status LEDs 1706, and one or more tray actuation feedback systems 1707 configured to actuate one or more trays 1708. The plate sampler 1700 may further include one or more of an AC voltage outlet 1709 or any other suitable power outlet, one or more communication ports 1710 configured to communicate with a computer system, and one or more communication ports 1711 configured to communicate with a robot, which may include a robotic arm or any type of robotic machinery. The plate sampler 1700 may further include one or more x-axis control and feedback systems 1712 for actuating the one or more trays 1708, one or more y-axis control and feedback systems 1713 for actuating the one or more trays 1708, and one or more z-axis control and feedback systems 1714 for actuating the one or more trays 1708.

Figure 18:
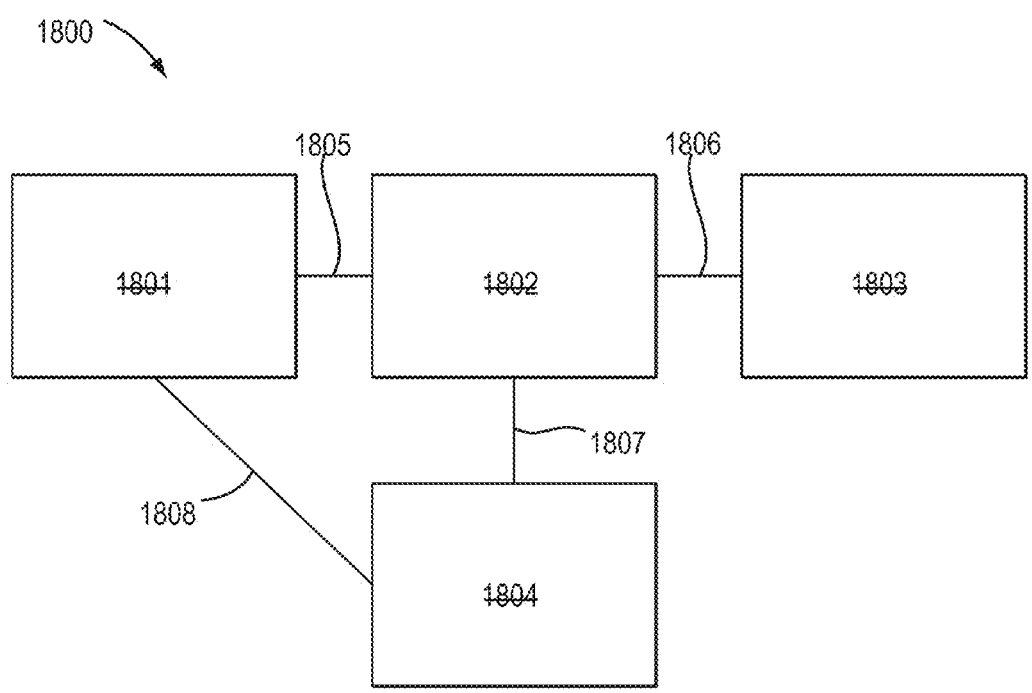
FIG. 18 illustrates an exemplary embodiment of a system for performing hi-throughput flow cytometry.

FIG. 18 illustrates an embodiment of a system 1800 for performing hi-throughput flow cytometry according to an embodiment of the present invention. The system 1800 may include a flow cytometer 1801, a plate sampler 1802, a robot or robotic machinery 1803 configured to manipulate sample plates, and a controller or computer system 1804 configured to control one or more of these components. The flow cytometer 1801 may be any flow cytometer known in the art. The robot or robotic machinery 1803 may be, for example, a robotic arm, or any other device capable of manipulating a sample plate automatically according to instructions corresponding to an experimental or industrial protocol. The controller or computer system 1804 may be a separate controller or a controller embedded in one of the flow cytometer 1801, the plate sampler 1802, and the robot or robotic machinery 1803. The controller or computer system 1804 may be any computer system known in the art, including a laptop computer, a desktop computer, and a workstation, and may in particular be any system including a bus, a processor coupled with the bus for processing information, and a memory (e.g., RAM, ROM) or other dynamic storage device for storing information and/or instructions to be executed by the processor.

Preferably, the flow cytometer 1801 may be an acoustic flow cytometer configured to acoustically focus a sample in a flowing fluid using acoustic energy. For example, the flow cytometer may be an acoustic flow cytometer embodying one or more of the teachings of any one or more of U.S. Pat. No. 7,340,957, issued Mar. 11, 2008, U.S. Pat. Appl. Pub. No. 2009/0050573, published Feb. 26, 2009, U.S. Pat. Appl. Pub. No. 2009/0053686, published Feb. 26, 2009, U.S. Pat. Appl. Pub. No. 2009/0029870, published Jan. 29, 2009, U.S.

Pat. Appl. Pub. No. 2009/0048805, published Feb. 19, 2009, U.S. Pat. Appl. Pub. No. 2009/0042239, published Feb. 12, 2009, U.S. Pat. Appl. Pub. No. 2009/0045107, published Feb. 19, 2009, U.S. Pat. Appl. Pub. No. 2009/0042310, published Feb. 12, 2009, U.S. Pat. Appl. Pub. No. 2009/0178716, published Jul. 16, 2009, U.S. Pat. Appl. Pub. No. 2008/0245709, published Oct. 9, 2008, U.S. Pat. Appl. Pub. No. 2008/0245745, published Oct. 9, 2008, U.S. Pat. Appl. Pub. No. 2009/0162887, published Jun. 25, 2009, U.S. Pat. Appl. Pub. No. 2009/0158823, published Jun. 25, 2009, and U.S. patent application Ser. No. 12/955,282, filed Nov. 29, 2010, the entire contents of every one of which being incorporated by reference herein.

The system 1800 may further include one or more fluidic connections 1805 between the flow cytometer 1801 and the plate sampler 1802, one or more a communications connections 1806 between the plate sampler 1802 and the robot or robotic machinery 1803, one or more a communications connections 1807 between the plate sampler 1802 and the controller or computer system 1804, and one or more communications connections 1808 between the flow cytometer 1801 and the controller or computer system 1804.

According to exemplary embodiments described herein, any of the foregoing plate samplers may include a sampling probe or system. FIGS. 19A-19E illustrate an exemplary sample probe 1900.

The sampling probe 1900 or system may include a non-ferrous housing 1902 to minimize interference with magnetic fields and sensors such as a Hall sensor 1904. The housing 1902 may also include an anodized aluminum housing to provide structural rigidity and corrosion resistance. In various embodiments described herein, the sampling probe 1900 may include a restorative spring 1906*a* 1906*b* 1906*c* 1906*e*. A restorative spring 1906*e* may include one magnet, for example. A one magnet restorative spring 1906*e*configuration of sample probe 1930 according to various embodiments is shown in FIG. 19E.

In other embodiments, a restorative spring 1906*a* 1906*b* 1906*c* includes at least three magnets. The restorative spring 1906*a* 1906*b* 1906*c* 1906*e* provides a magnetic field for sensing purposes and for providing a restorative spring restoring force to return the probe to a relaxed position. In some embodiments, the sampling probe 1900 may include at least three magnets.

According to various embodiments described herein, the restorative spring may include a single magnet, three magnets, a plurality of magnets, or a metal restorative spring, for example. It should be recognized that the restorative spring according to various embodiments described herein may be any object or assembly that can provide sufficient restorative force to return the probe to a relaxed position.

The magnet or magnets of the restorative spring 1906*a* 1906*b* 1906*c* 1906*e* may be of any magnet type. For example, the magnets may be rare earth magnets to provide for denser field strength and longer magnetic life. The sampling probe 1900 or system may also include a Hall effect sensor 1904 to detect magnetic field changes as magnets are pushed together or allowed to more apart. The probe 1908 may be used for drawing samples from a sample plate. The probe 1908 may be moved by interference with an obstructing object upon detection of changes in Hall effect sensor readings by the Hall effect sensor 1904 so as to retract the probe 1908 from the obstructing object and avoid damage to the probe 1908.

According to exemplary embodiments of the present teachings, the probe 1908 may normally be in an extended position with opposing magnets forcing themselves apart and thereby driving the probe 1908 to the extended position. The Hall effect sensor 1904 may transmit a signal relative to the field strength generated by the restorative spring 1906*a* 1906*b* 1906*c* 1906*e* in the extended position. As the probe 1908 is moved toward the sample plate and comes in contact with a surface, the opposing magnets of the restorative spring 1906*a* 1906*b* 1906*c* are forced together, thereby increasing the field strength sensed by the Hall effect sensor 1904 and changing the signal from the Hall effect sensor 1904.

This change in signal may be interpreted by the software as motion of the probe 1908 relative to the rest of the system. The software may then stop the motion of the probe 1908 so that the probe 1908 is not damaged by being forced against the interfering object.

According to exemplary embodiments of the present invention, the probe 1908 may be magnet-based and may use a Hall effect sensor 1904, which may improve reliability and sealing. Although the sensor may be a Hall effect sensor 1904 that uses a magnetic field for detection, to sense, react, and stop in the event of unexpected contact, any sensor that can sense the displacement of the probe once in contact with a surface could also be used. For example, capacitive, impedance, optical, displacement, pressure, etc, sensors could also be used. Further, although the restoring force for the probe may be magnet-based, other restoring forces may also be used, including a restorative spring, an inductive force generator, or other mechanisms to impose a restoring force on the probe. Magnetic repulsion, however, is particularly useful as it provides a soft restorative force and increases sensor sensitivity by compacting field lines.

According to exemplary embodiments of the present disclosure, when the probe 1908 is retracted from the interfering object, software may sense the Hall effect signal returning to the steady state value. When the system is in a resting position, the software may calibrate the steady state to the Hall effect signal value, and any changes in magnetic field, position of the probe, or Hall effect sensor may be calibrated out every time the system returns to a rest position. This also allows the probe 1908 to track and discard any drift in the electronic signal that can occur over longer time periods. Further, knowledge that the probe 1908 may have touched an object may be used to calibrate all three dimensions of the system. This may be done by moving the probe to a series of known locations with unique three-dimensional coordinates. As the probe touches each known location, the system can calibrate the current position to the known coordinates of that position. Then, by touching several locations, the system can calibrate location in all three operational axes.

According to an exemplary embodiment of the present teachings, there is provided a sampling probe 1900, including: a fitting 1910; an elongated portion extending from the fitting; and a restorative spring 1906*a* 1906*b* 1906*c* including a plurality of magnets inserted onto the elongated portion.

In such a sampling probe, the fitting 1910 may include a substantially cylindrical portion having an external teethed surface. The elongated portion may include an interior channel. The restorative spring 1906*e* may include a single magnet. In other embodiments, the restorative spring 1906*a* 1906*b* 1906*c* includes at least three magnets. The restorative spring 1906*a* 1906*b* 1906*c* may include at least two magnets having a polarity oriented along a first direction and at least one additional magnet having a polarity oriented along a direction opposite to the first direction. At least one of the at least three magnets may be a rare earth magnet. The magnets may be a rare earth magnet. In some embodiments, the sampling probe 1900 may preferably not include art optical sensor, a non-magnetic metal restorative spring, a strain gage, and electrical contacts. The properties of the Hall effect sensor 1904 and the restorative spring 1906*a* 1906*b* 1906*c* 1906*e* may be selected to allow the restorative spring 1906*a* 1906*b* 1906*c* 1906*e* to provide a restorative force allowing sensing of an obstacle and stopping without damaging a tip of the sampling probe 1900.

Furthermore, when an obstacle is detected, the user may be notified that there was an obstacle and that sampling should not proceed. An error may also be generated and indicated to the user.

According to an exemplary embodiment of the present teachings, there is provided a sampling system, including: a housing 1902; a Hall effect sensor 1904 mounted with screws 1912 onto the housing 1902; and a probe 1908 inserted into the housing 1902, the 1908 probe including an elongated portion and a plurality of magnets, comprising a restorative spring 1906*a* 1906*b* 1906*c* 1906*e*, inserted onto the elongated portion. In various embodiments described herein, the plurality of magnets may comprise a single magnet. In other embodiments, the plurality of magnets may include more than one magnet.

The plurality of magnets may include at least three magnets. The plurality of magnets may include at least two magnets having a polarity oriented along a first direction and at least one additional magnet having a polarity oriented along a direction opposite to the first direction. Each of the at least three magnets may be a rare earth magnet.

In such a sampling system, the housing 1902 may be selected from one of a non-ferrous housing and an anodized aluminum housing. The sampling probe 1900 may include a fitting 1910 including a substantially cylindrical portion having an external teethed surface. The elongated portion may include an interior channel. The sampling probe 1900 may preferably not include an optical sensor, a non-magnetic metal spring, a strain gage, and electrical contacts. The sampling probe or system 1900 may further include an analog sensor configured to allow sampling probe drift compensation via calibration of an axis of the sampling probe. The sampling system 1900 may further include a controller configured to control a movement of the sampling probe 1900 using a stroke of between about 2.5 mm and about 4.5 mm, the stroke including between about 0.75 mm and about 1.25 mm for sensing and between about 0.75 mm and about 1.25 mm for stopping. The stroke may further include between about 0.75 mm and about 1.25 mm for movement noise. The stroke may further include between about 0.25 mm and about 0.75 mm for overstroke.

Figure 9:
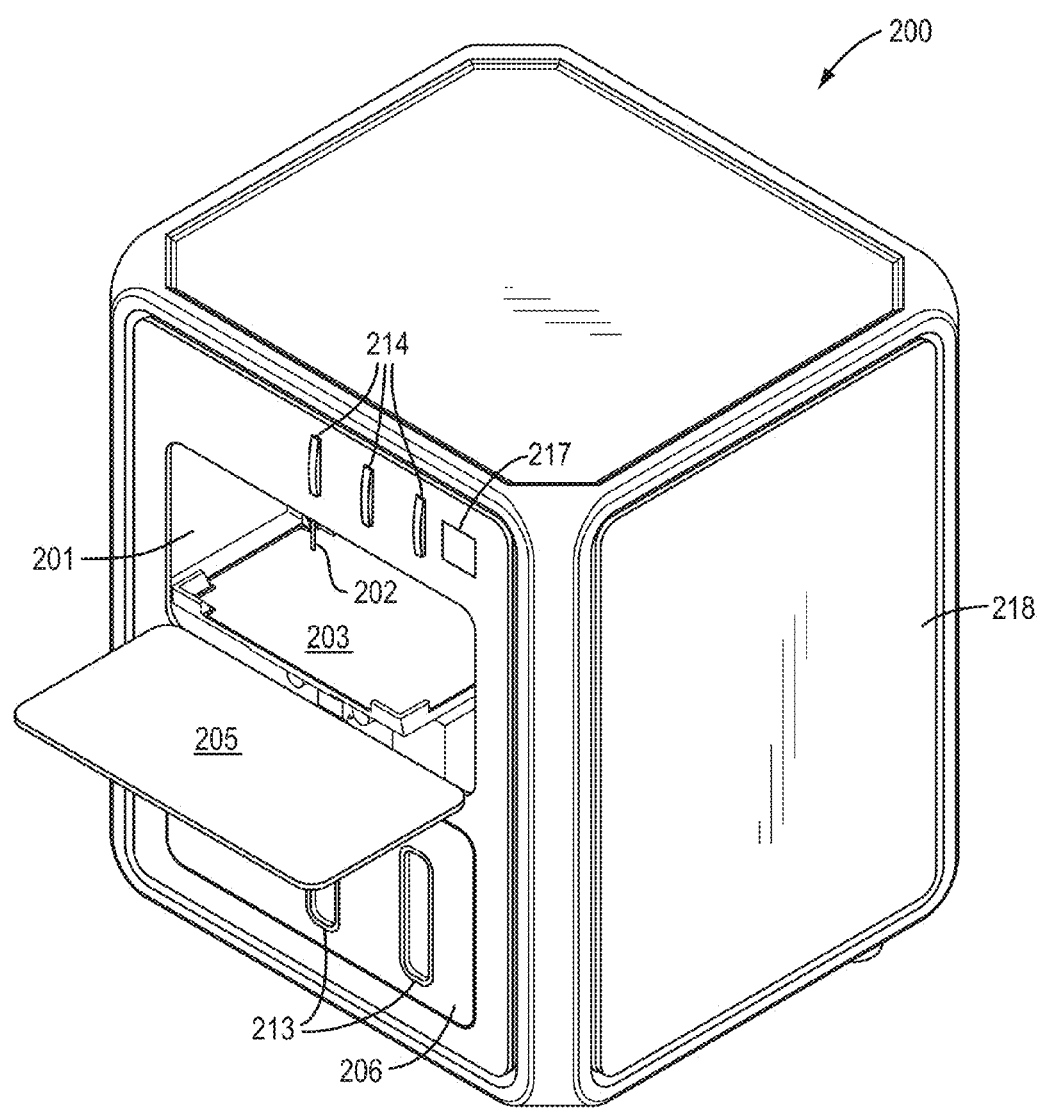
FIG. 9 is a perspective view of another exemplary plate sampler.
Figure 10:
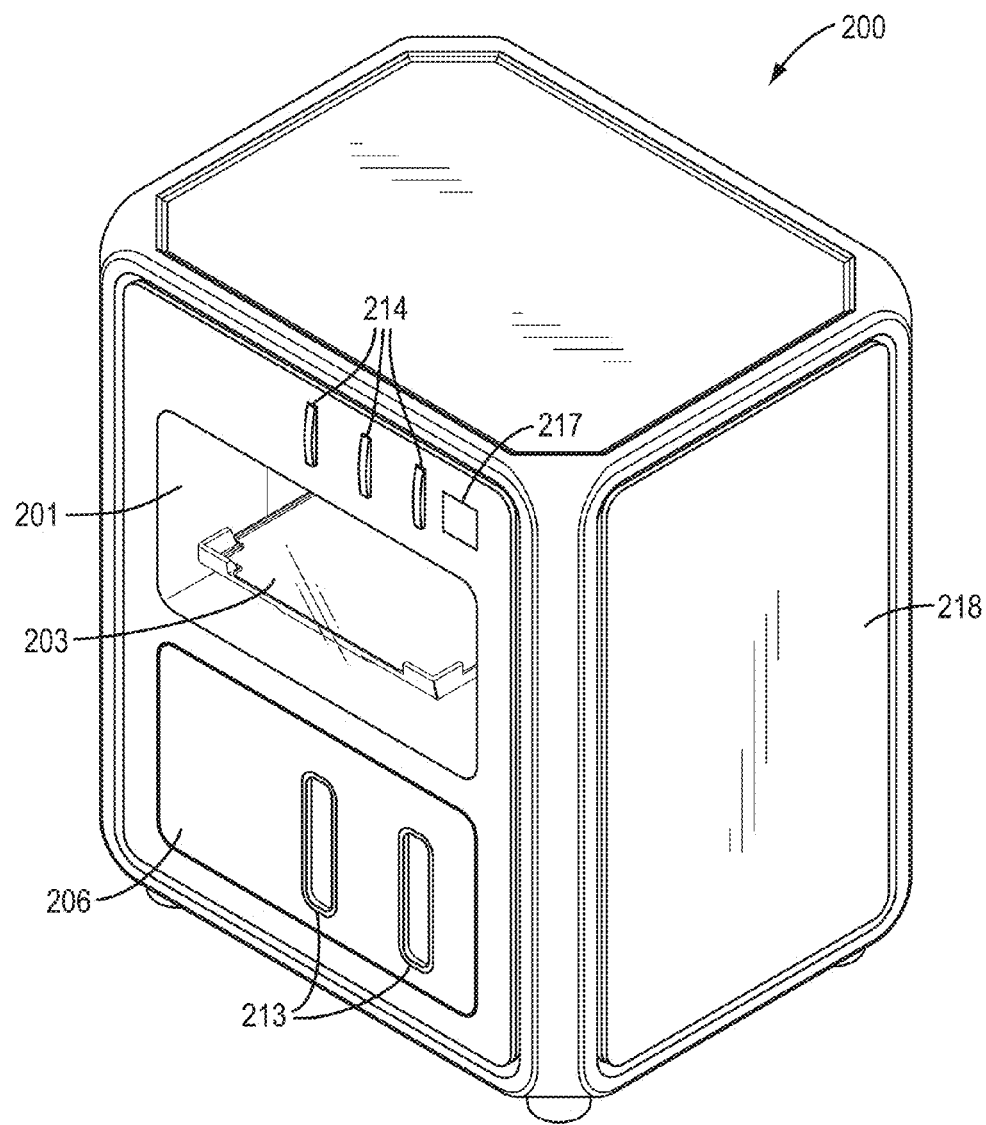
FIG. 10 is another perspective view of the exemplary plate sampler set forth in FIG. 9.
Figure 11:
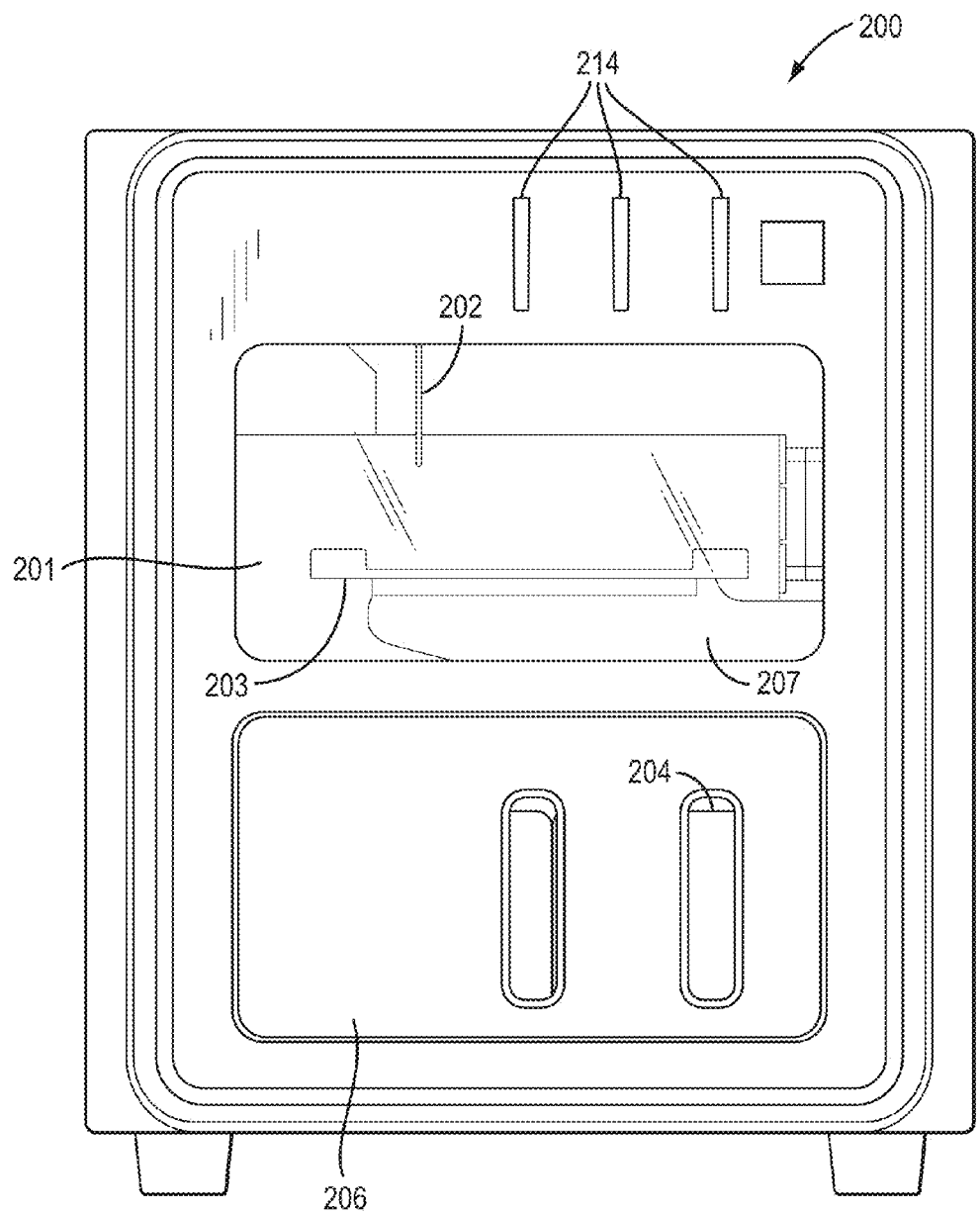
FIG. 11 is a front view of the exemplary plate sampler set forth in FIG. 9.
Figure 12:
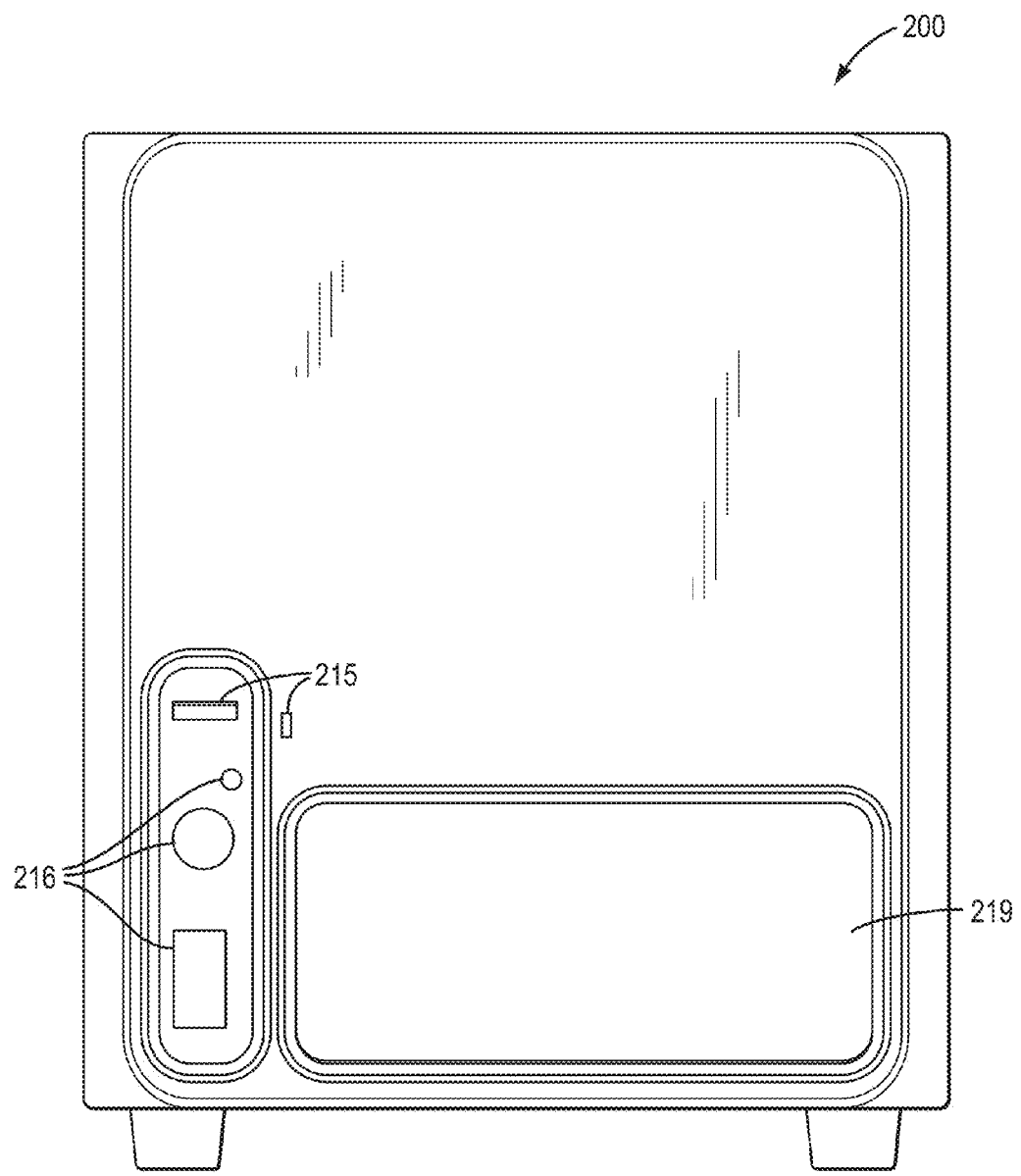
FIG. 12 is a back view of the exemplary plate sampler set forth in FIG. 9.
Figure 13:
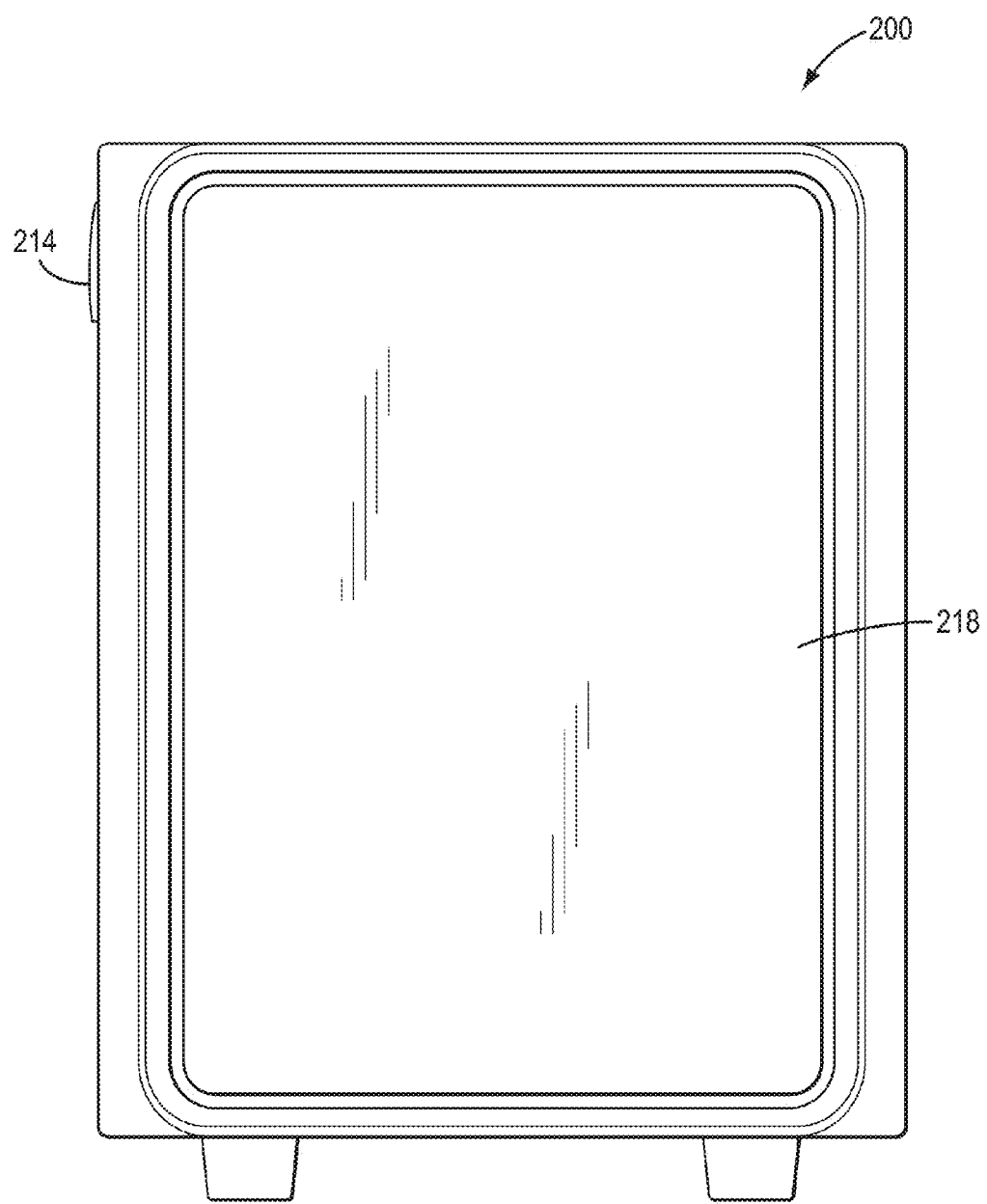
FIG. 13 is a side view of the exemplary plate sampler set forth in FIG. 9.
Figure 14:
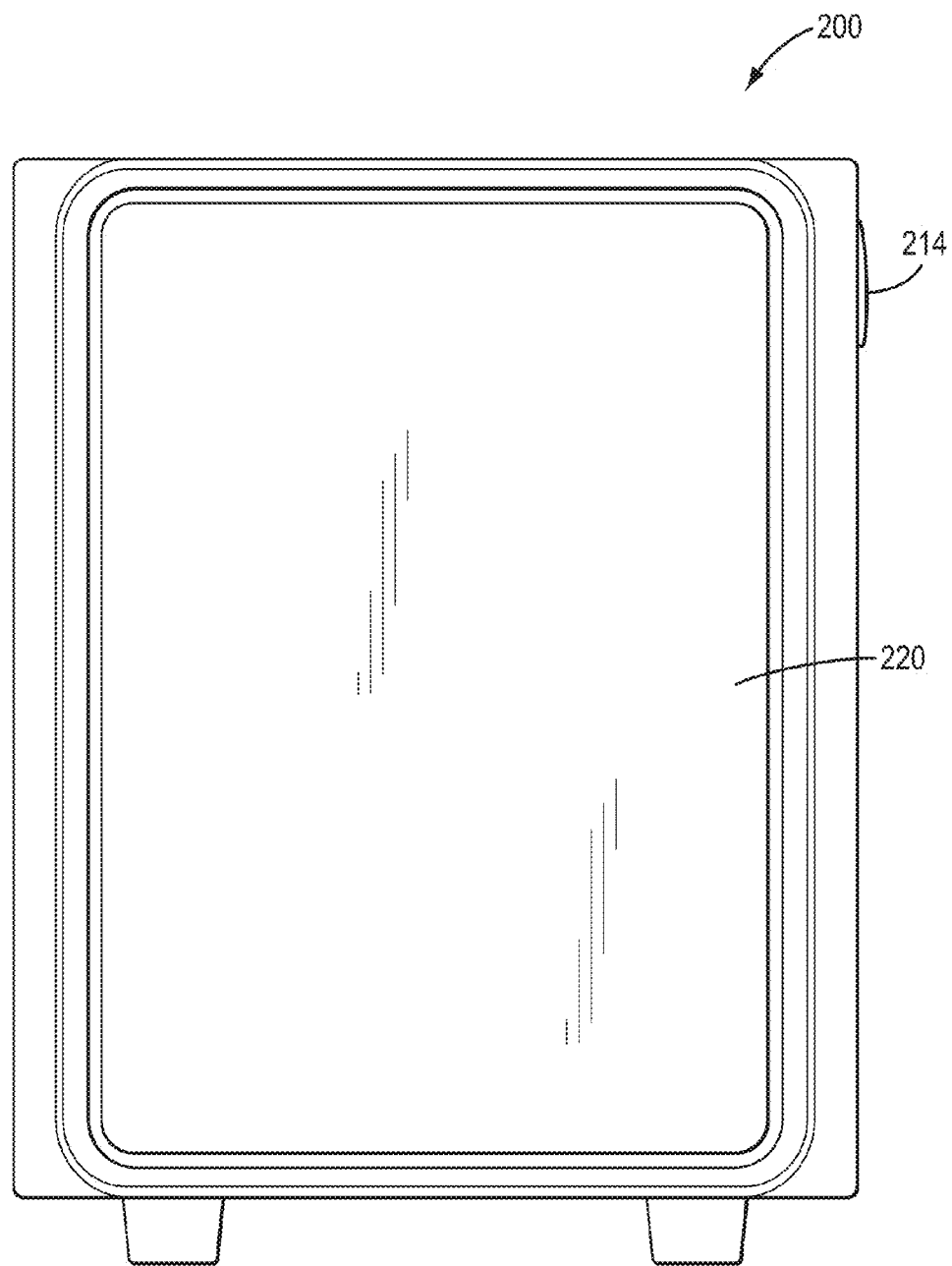
FIG. 14 is another side view of the exemplary plate sampler set forth in FIG. 9.
Figure 15:
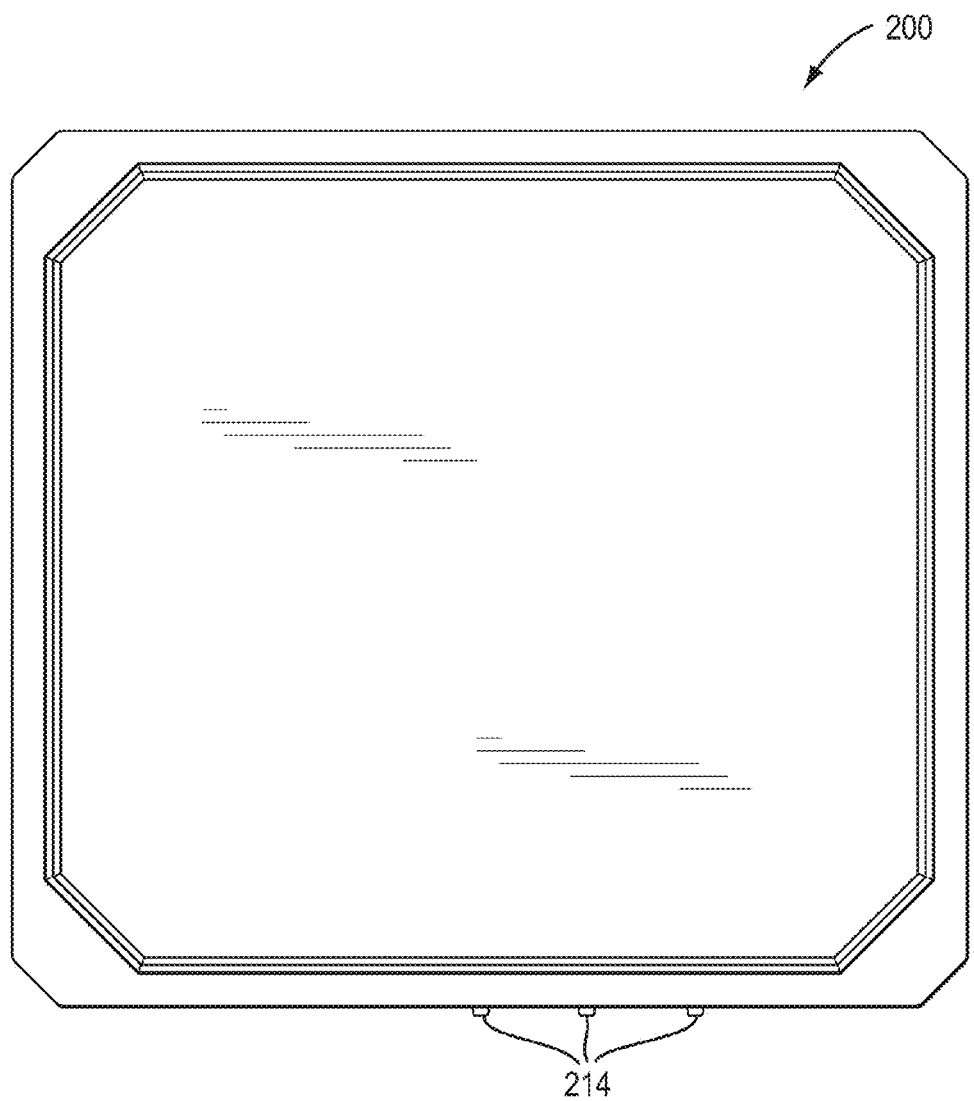
FIG. 15 is a top view of the exemplary plate sampler set forth in FIG. 9.
Figure 16:
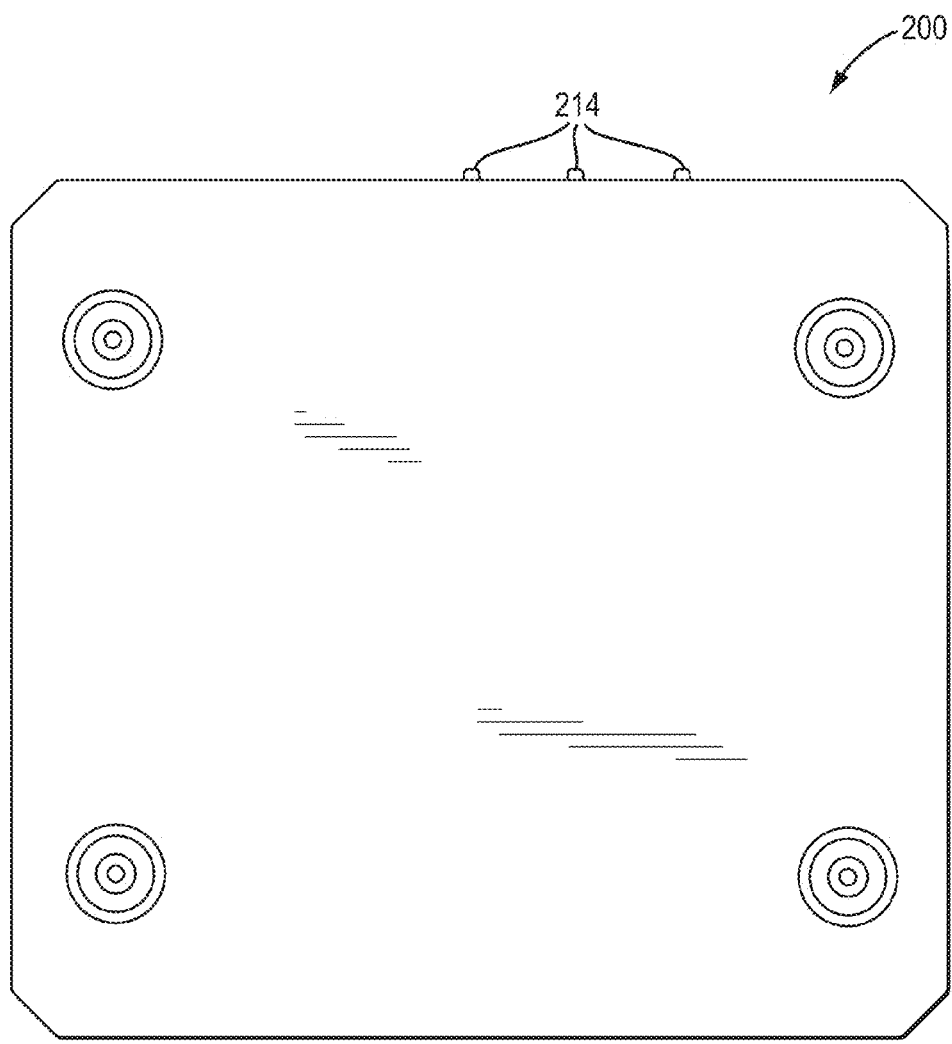
FIG. 16 is a bottom view of the exemplary plate sampler set forth in FIG. 9.

With reference to FIG. 9, according to an exemplary embodiment of the present teachings, there is provided a plate sampling apparatus 200, including: a sampling compartment 201 including a tray 203 configured to receive a sample plate configured to include a plurality of samples; and a probe 202 configured to obtain a sample from the sample plate, the probe including a fitting, an elongated portion extending from the fitting, and a restorative spring including a plurality of magnets inserted onto the elongated portion. The plate sampling apparatus 200 may further include a Hall effect sensor.

According to an exemplary embodiment of the present teachings, there is provided a hi-throughput cytometry system, including: a flow cytometer configured to acoustically focus a sample in a flowing fluid; and a plate sampler in fluidic communication with the flow cytometer, the plate sampler including: a sampling compartment including a tray configured to receive a sample plate configured to include a plurality of samples, and a probe (FIG. 19A) configured to obtain a sample from the sample plate, the sample probe 1900 including a fitting 1910, an elongated portion extending from the fitting, and a restorative spring 1906*a* 1906*b* 1906*c* 1906*e* inserted onto the elongated portion. The plate sampler may further include a Hall effect sensor 1904.

Figure 19A:
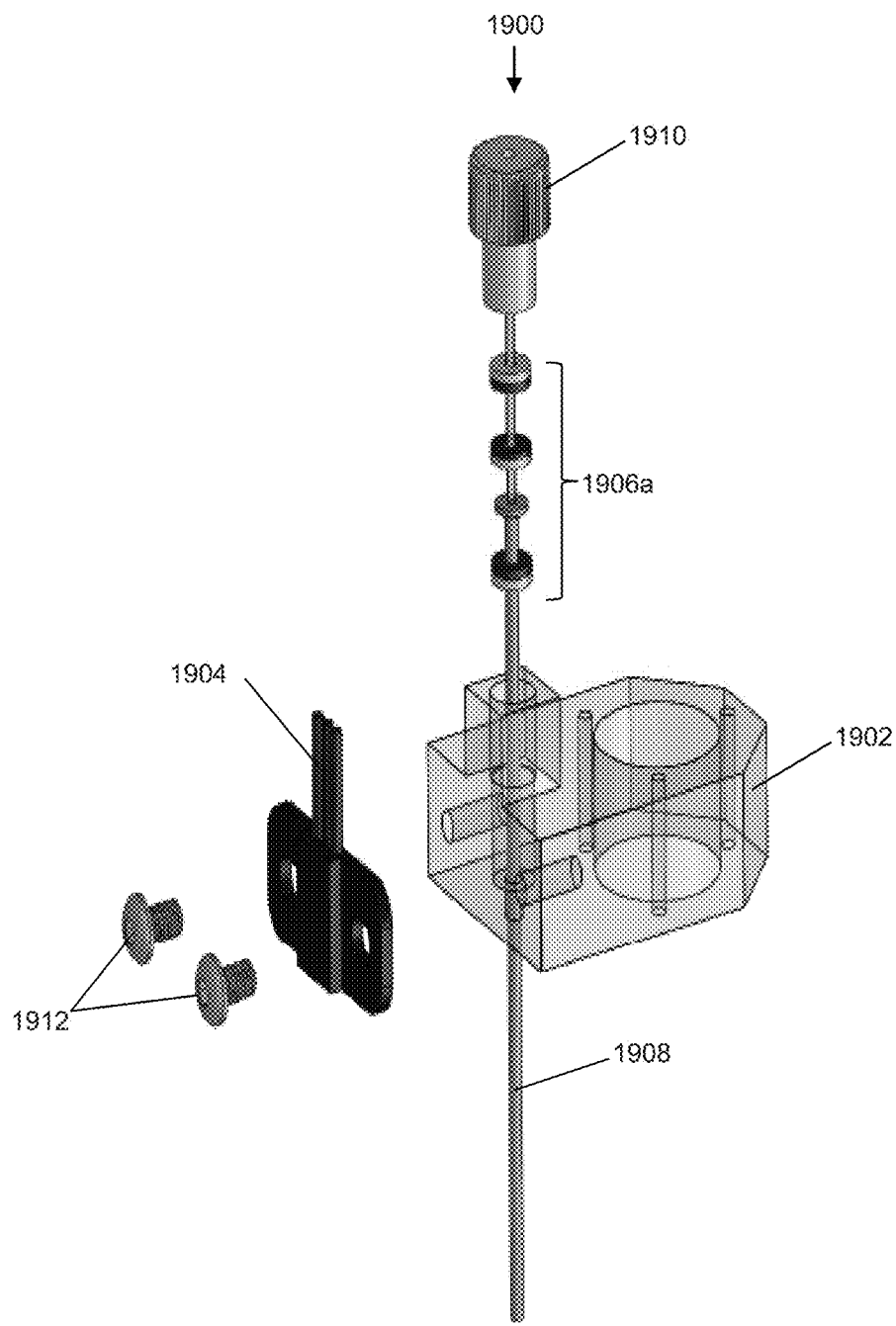
FIGS. 19A-19E illustrates exemplary embodiments of sampling probes and systems.
Figure 19B:
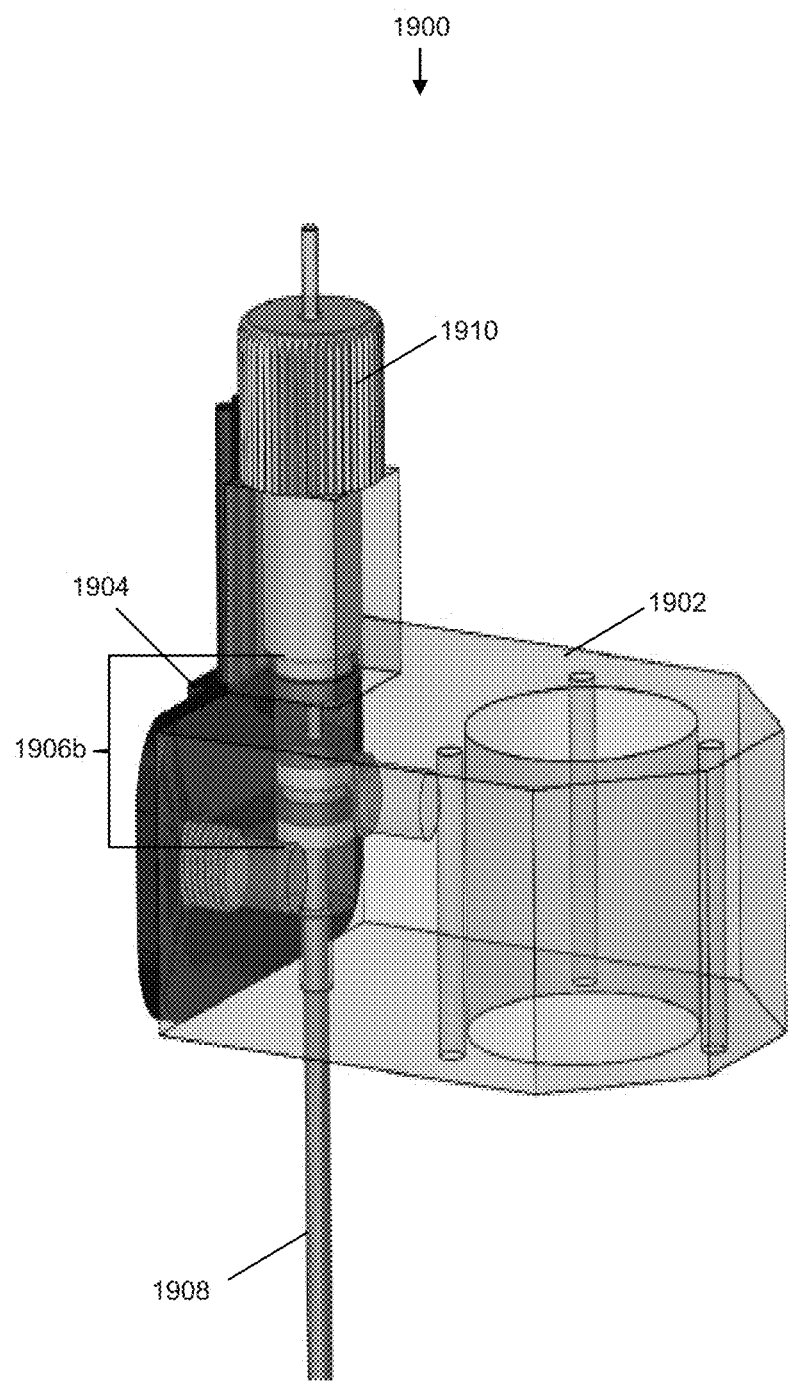
Figure 19C:
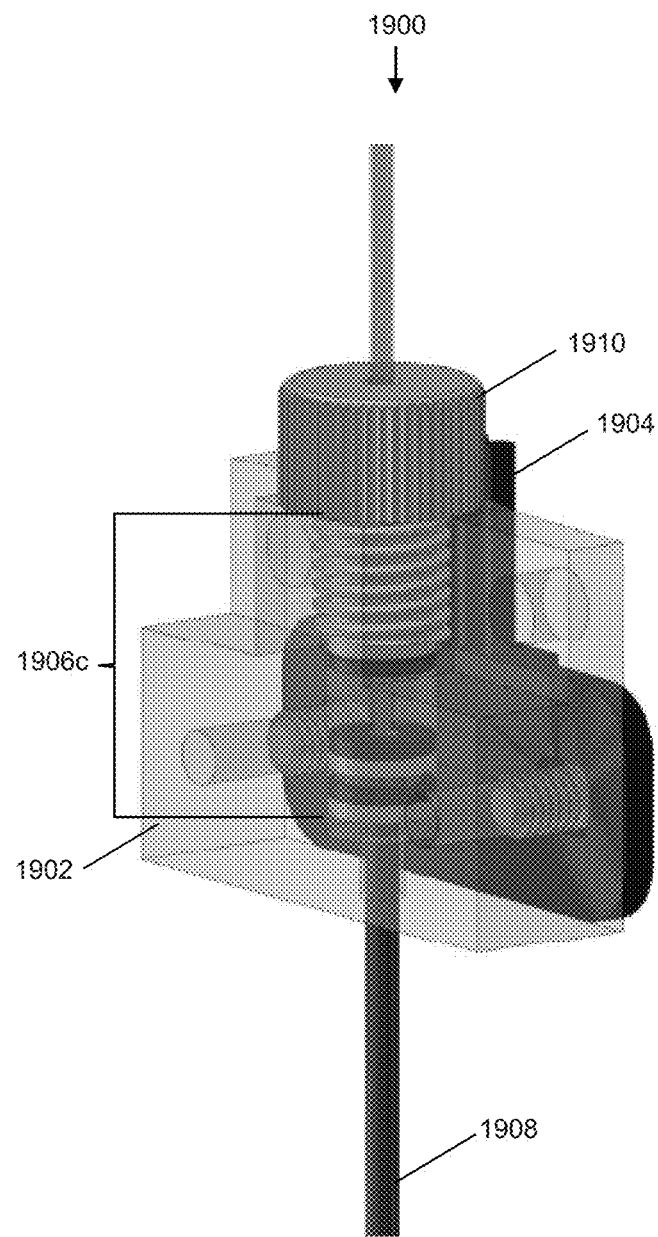
Figure 19D:
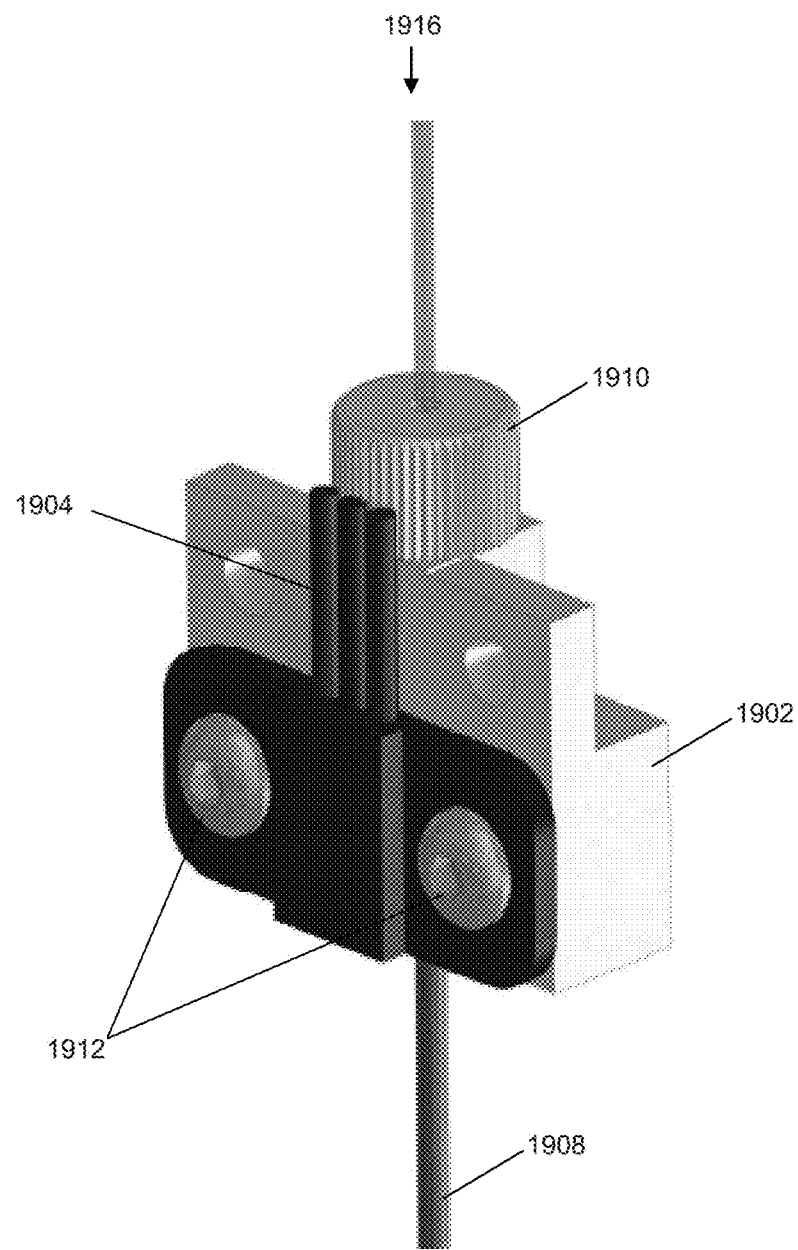
Figure 19E:
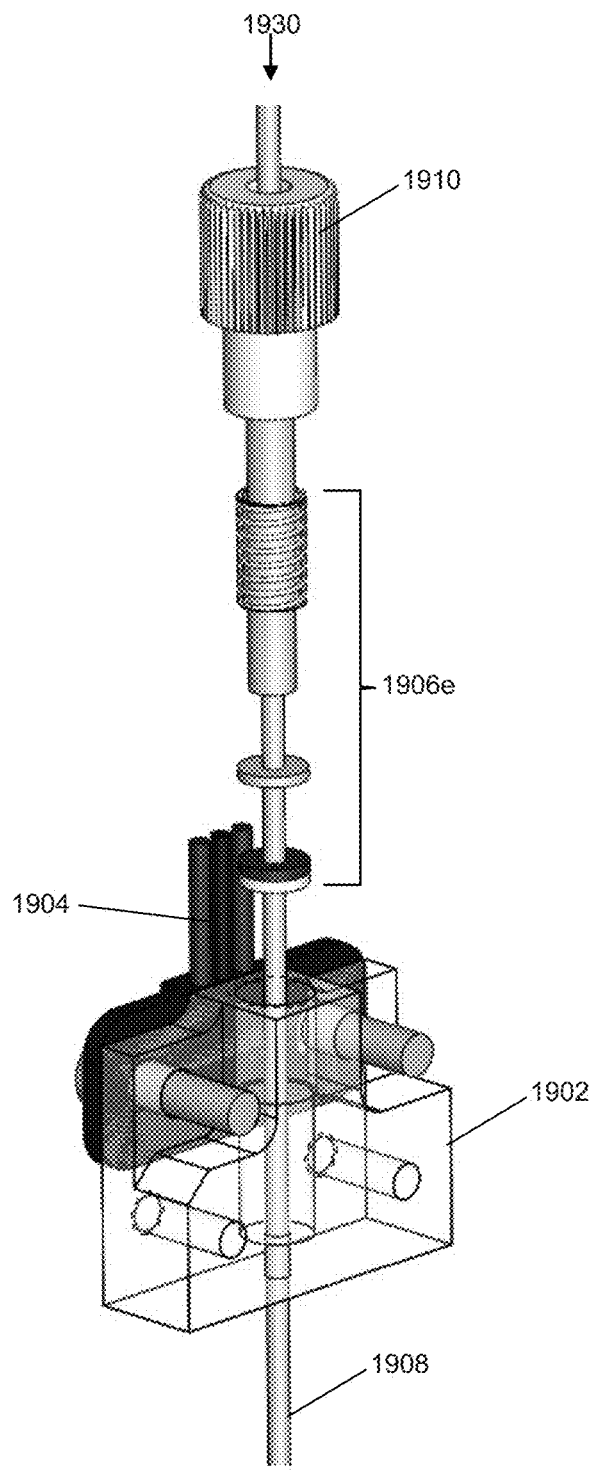

According to an exemplary embodiment of the present teachings, with reference to FIG. 19A, there is provided a method for obtaining a sample, including: sampling a sample plate including one or more samples in a plate sampler; moving toward the sample plate a probe including a fitting 1910, an elongated portion extending from the fitting 1910, and a restorative spring 1906*a* 1906*b* 1906*c* including at least two opposing magnets inserted onto the elongated portion; sensing a field strength generated by the opposing magnets in the extended position using a Hall effect sensor 1904; detecting an increase in the field strength generated by the opposing magnets using the Hall effect sensor 1904; stopping the motion of the probe 1908 toward the sample plate; and obtaining a sample from the one or more samples in the sample plate using a probe 1908 including a fitting 1910, an elongated portion extending from the fitting 1910, and a restorative spring 1906*a* 1906*b* 1906*c* including a plurality of magnets inserted onto the elongated portion.

Such a method may further include controlling a movement of the probe using a stroke of between about 2.5 mm and about 4.5 mm, the stroke including between about 0.75 mm and about 1.25 mm for sensing, between about 0.75 mm and about 1.25 mm for stopping, between about 0.75 mm and about 1.25 mm for movement noise, and between about 0.25 mm and about 0.75 mm for overstroke. It may also include magnetically retracting the probe upon detection of the increase in the field strength generated by the opposing magnets using the Hall effect sensor. And it may include generating a dimensional calibration signal upon detection of the increase in the field strength generated by the opposing magnets using the Hall effect sensor, and calibrating probe locations along three operational axes.

According to an exemplary embodiment of the present teachings, there is provided a method for making a sampling probe, including: providing a fitting; assembling onto the fitting an elongated portion extending from the fitting; and inserting onto the elongated portion a restorative spring including a plurality of rare earth magnets.

In such a plate sampling apparatus, a plate sampler may include: a loading compartment including a sample probe and a tray, the tray being configured to receive a sample plate configured to include a plurality of samples; a fluidic compartment configured to receive one or more fluid containers; a first access door configured to allow access to the loading compartment; and a second access door configured to allow access to the fluidic compartment.

The loading compartment may further include an actuation mechanism configured to move the tray. The actuation mechanism may be configured to move the tray, when the first access door is opened, along a direction substantially perpendicular to a direction of gravity between a first position located within the loading compartment and a second position located at least partly outside the loading compartment such that a sample plate may be loaded onto the tray from a side of the apparatus. Alternatively, the actuation mechanism is configured to move the tray, when the first access door is opened, along a direction substantially parallel to a direction of gravity between a first position located within the loading compartment and a second position located at least partly outside the loading compartment such that a sample plate may be loaded onto the tray from above the apparatus.

One or more side portions of the first access door may include one or more indentations configured to hold the tray in place in the second position. A top surface of the apparatus surrounding the first access door may include a recessed area configured to contain spilled fluid. The tray may include a plurality of protruding corners configured to hold a sample plate in place within the tray.

The system may further comprise robotic machinery configured to transfer one or more fluids and samples to and from one or more sample plates and further configured to spatially manipulate the one or more sample plates so as to insert the one or more sample plates in the tray of the plate sampler; and a controller configured to control the flow cytometer, the plate sampler, and the robotic machinery according to one or more experimental protocols.

According to an exemplary embodiment of the present teachings, there is provided a hi-throughput cytometry system, including: a flow cytometer; and a plate sampler in fluidic communication with the flow cytometer, the plate sampler including: a sample probe and a tray, the tray being configured to receive a sample plate configured to include a plurality of samples; a fluidic compartment configured to receive one or more fluid containers; a first access door configured to allow access to the loading compartment; and a second access door configured to allow access to the fluidic compartment.

According to an exemplary embodiment of the present teachings, there is provided a hi-throughput cytometry system, including: a flow cytometer; and a plate sampler in fluidic communication with the flow cytometer, the plate sampler including an actuation mechanism configured to move a tray toward a top surface of the plate sampler such that a sample plate may be loaded onto the tray from above the plate sampler.

Furthermore, as mentioned above, to provide precise positioning of the sample probe in relation to the sample plate, the sampling device may need to detect, with a high degree of accuracy, the positional relationship between each of its' three axes and the physical position of the sample plate. Because of variations in manufacturing and wear of the axes over time, it is important that the sampling device may also be able to calibrate itself on a periodic basis, to determine the values that correspond to these physical relationships. A sample probe in accordance with embodiments described herein provides a mechanism by which the sampling probe can more accurately determine the position of the sampling probe in relation to the sample plate.

Figure 20A:
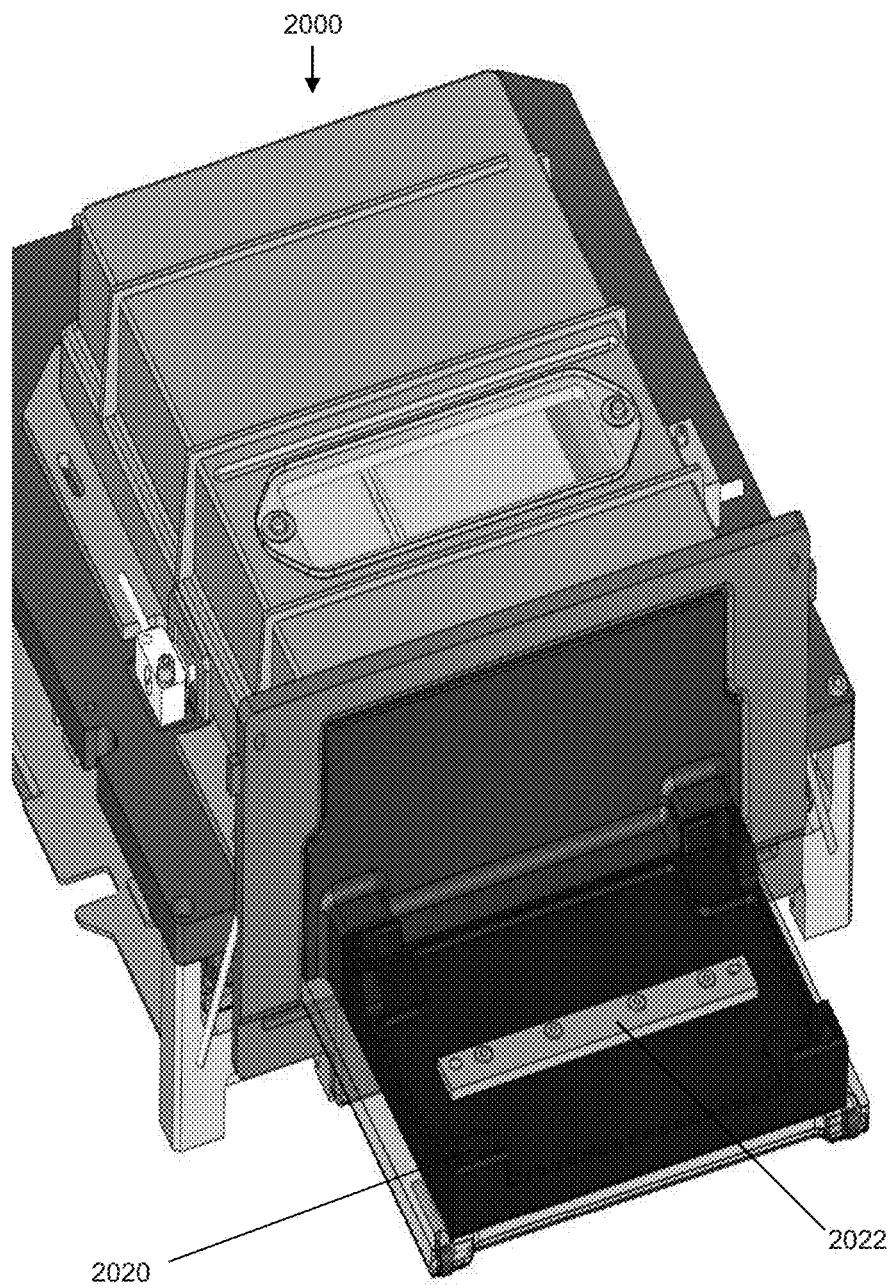
FIGS. 20A-20B illustrates exemplary embodiments of a system with a calibration target.
Figure 20B:
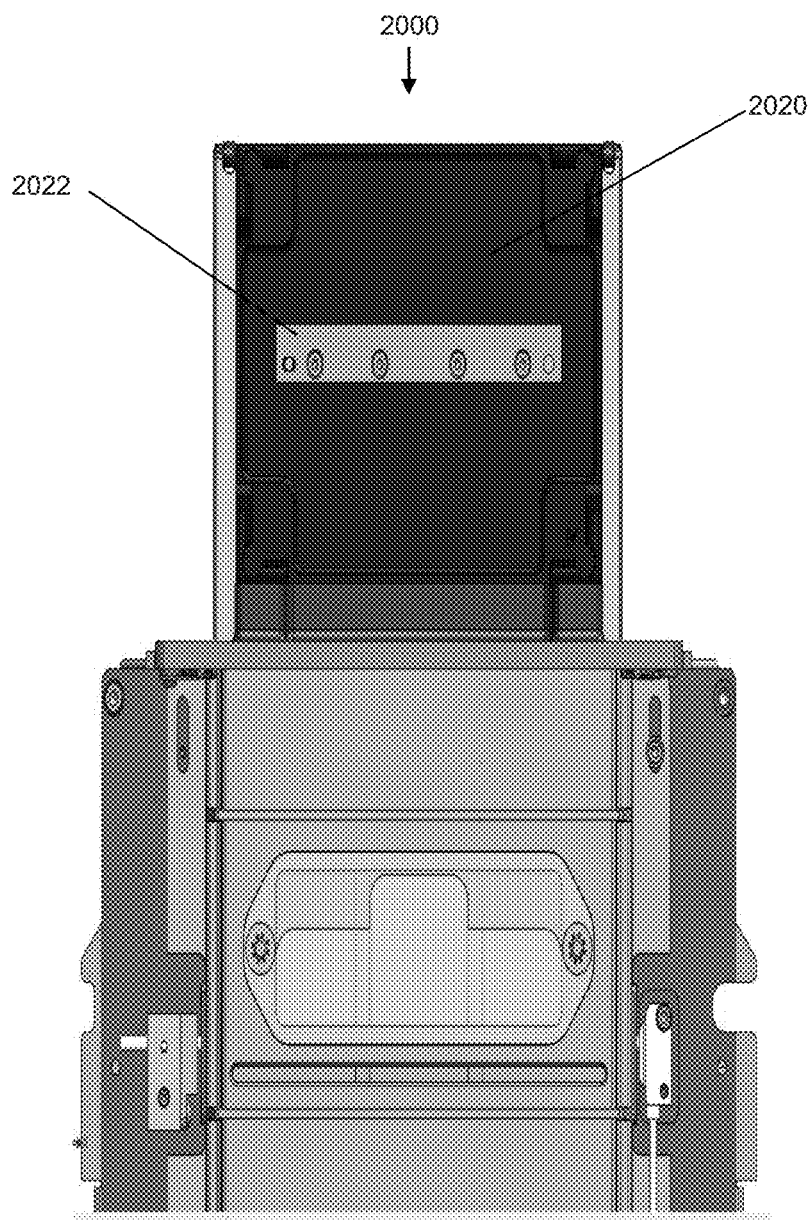
Figure 21:
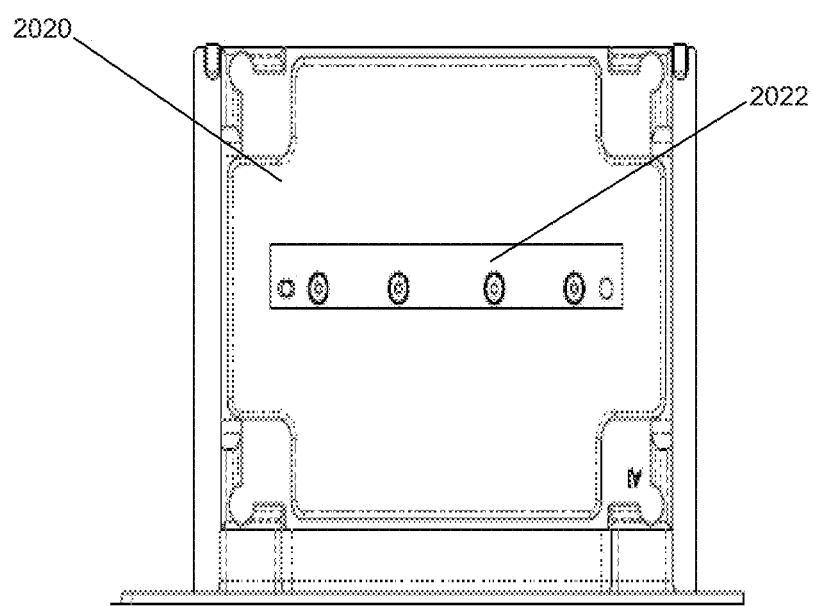
FIG. 21 illustrates an exemplary embodiment of a tray with a calibration target.

FIGS. 20A and 20B illustrate an exemplary plate sampler apparatus 2000 with a calibration target 2022. FIG. 21 illustrates an exemplary tray 2020 with a calibration target 2022. A calibration target 2022 at a known position in the tray 2020 which holds the sample plate, and having the calibration target 2022 at a position able to be contacted by the sample probe, may be able to extrapolate the position of the sample probe in relation to a plate resting in the tray 2020.

Since the sample probe provides feedback when it is displaced in the Z-axis, by extending the probe along the Z-axis while monitoring displacement, it provides a means to determine the distance between the Z-axis origin point and the calibration target 2022. By creating a calibration target 2022 of known dimensions and locating it precisely at a known position in the tray 2020, it may be possible to use displacement of the probe in the Z-axis to determine position of the probe in the X-Y plane.

An example calibration method is described below according to various embodiments of the present teachings. First, the sample probe is positioned over the approximate center of the calibration target 2022. The sample probe is moved downward until displacement indicates the probe has contacted the calibration target 2022. This may indicate relative height of the calibration target 2022 in relation to the tray. Next, the sample probe is moved along the Y-axis a distance of 4 mm. The sample probe is extended downward again. The displacement is used to determine if the sample probe is still over the calibration target 2022 or has moved off the edge. These steps are repeated until the edge of the calibration target 2022 has been detected.

Further, the sample probe may be moved in the Y-axis back over the calibration target a distance of 8 mm. This can be repeated using shorter steps of 250 um to provide finer resolution of the sample probe position. Once the calibration target 2022 edge has been determined to the desired accuracy along the Y-axis, the sample probe can be moved along the X-axis.

A similar process in the X-axis is repeated until the calibration target 2022 edge has been determined in the X-axis. In this way, the method may provide the X, Y coordinates, relative to the X-Y axes of motion, of a corner of the calibration target 2022 which is at a known location on the tray 2020. Using these coordinates, the location of the calibration target 2022, and the dimensions of the tray 2020, a relationship between the sample probe and the sample tray 2020 can be determined.

Also, by utilizing a calibration target 2022 that spans the majority of the tray width 2020, and performing this calibration function across the entire calibration target 2022, it may be possible to detect any discrepancy between the X-Y orientation of the tray 2020 and the X-Y orientation of the axes of motion. If this discrepancy is known, it may be possible to compensate for it when positioning the sample probe. Thus, this may allow for accurate positioning of the sample probe on a sample plate even when the mechanical aspects of the system are not in correct alignment.

Embodiments of the present invention may be useful in one or more of basic research, pharmaceutical research, and industrial research. Further, they may be especially useful for performing one or more of intracellular immunophenotyping, extracellular immunophenotyping, fluorescent protein analysis, and cell proliferation analysis.

Other embodiments of the invention will be apparent to one of ordinary skill in the art having had the benefit of the present specification and/or having practiced one or more embodiments of the invention. Further, the present specification including the drawings are all exemplary and are not in any way limiting of the scope of the invention, which shall be determined by the following claims.

The invention claimed is:
1. A sampling probe comprising:
a fitting;
an elongated portion extending from the fitting;
a restorative spring including at least one ring-shaped magnet and a metal spring inserted onto exterior of the elongated portion; and
a Hall effect sensor wherein the properties of the Hall effect sensor and the at least one magnet are selected to allow the restorative spring to provide a restorative force allowing sensing of an obstacle and stopping without damaging a tip of the sampling probe.

2. The sampling probe of claim 1, wherein the fitting includes a substantially cylindrical portion having an external teethed surface.

3. The sampling probe of claim 1, wherein the elongated portion includes an interior channel.

4. The sampling probe of claim 1, wherein the at least one magnet is a rare earth magnet.

5. The sampling probe of claim 1, wherein the sampling probe does not comprise an optical sensor.

6. The sampling probe of claim 1, wherein the sampling probe does not comprise a strain gage.

7. The sampling probe of claim 1, wherein the sampling probe does not comprise electrical contacts.

8. The sampling probe of claim 1, further comprising a processor configured to execute machine readable instructions to interpret a signal transmitted from the Hall effect sensor.

\* \* \* \* \*